(12) United States Patent
Smith et al.

(10) Patent No.: US 11,097,095 B2
(45) Date of Patent: Aug. 24, 2021

(54) COCHLEAR IMPLANTS, MAGNETS FOR USE WITH SAME AND MAGNET RETROFIT METHODS

(71) Applicant: ADVANCED BIONICS AG, Staefa (CH)

(72) Inventors: James George Elcoate Smith, Santa Clarita, CA (US); Sarah Elizabeth Clabeaux, Ventura, CA (US)

(73) Assignee: Advanced Bionics AG, Staefa (CH)

( * ) Notice: Subject to any disclaimer, the term of this patent is extended or adjusted under 35 U.S.C. 154(b) by 154 days.

(21) Appl. No.: 16/499,311

(22) PCT Filed: Apr. 10, 2018

(86) PCT No.: PCT/US2018/026978
§ 371 (c)(1),
(2) Date: Sep. 29, 2019

(87) PCT Pub. No.: WO2018/191314
PCT Pub. Date: Oct. 18, 2018

(65) Prior Publication Data
US 2021/0106815 A1 Apr. 15, 2021

Related U.S. Application Data

(63) Continuation-in-part of application No. PCT/US2017/027041, filed on Apr. 11, 2017.

(51) Int. Cl.
*A61N 1/05* (2006.01)
*A61N 1/372* (2006.01)
(Continued)

(52) U.S. Cl.
CPC ........... *A61N 1/0541* (2013.01); *A61N 1/375* (2013.01); *A61N 1/37223* (2013.01);
(Continued)

(58) Field of Classification Search
CPC .. A61N 1/0541; A61N 1/37223; A61N 1/375; A61N 1/36036; A61N 1/3758;
(Continued)

(56) References Cited

U.S. PATENT DOCUMENTS 4,214,366 A 7/1980 Laban
4,352,960 A 10/1982 Dormer et al.
(Continued)

FOREIGN PATENT DOCUMENTS

EP 2117489 B1 5/2010
EP 2853287 A1 4/2015
(Continued)

OTHER PUBLICATIONS

PCT International Search and Written Opinion dated Jul. 2, 2018 for PCT App. Ser. No. PCT/US2018/026978.
(Continued)

*Primary Examiner* — Amanda K Hulbert
*Assistant Examiner* — Natasha Patel
(74) *Attorney, Agent, or Firm* — Henricks Slavin LLP

(57) ABSTRACT

A cochlear implant exomagnet that includes a magnet apparatus and a magnet mount configured to secure the magnet apparatus to a cochlear implant in such a manner that the magnet apparatus is not located within the internal magnet pocket of the cochlear implant.

23 Claims, 15 Drawing Sheets

(51) Int. Cl.
*A61N 1/375* (2006.01)
*H04R 25/00* (2006.01)

(52) U.S. Cl.
CPC ......... *H04R 25/505* (2013.01); *H04R 25/554* (2013.01); *H04R 2225/51* (2013.01); *H04R 2225/67* (2013.01)

(58) Field of Classification Search
CPC ...... A61N 1/08; H04R 25/505; H04R 25/554; H04R 2225/51; H04R 2225/67
See application file for complete search history.

(56) References Cited

U.S. PATENT DOCUMENTS

| | | |
|---|---|---|
| 4,595,390 A | 6/1986 | Hakim et al. |
| 4,606,329 A | 8/1986 | Hough |
| 4,612,915 A | 9/1986 | Hough et al. |
| 4,618,949 A | 10/1986 | Lister |
| RE32,947 E | 6/1989 | Dormer et al. |
| 5,290,281 A | 3/1994 | Tschakaloff |
| 5,755,762 A | 5/1998 | Bush |
| 5,824,022 A | 10/1998 | Zilberman et al. |
| 5,945,762 A | 8/1999 | Chen et al. |
| 6,032,677 A | 3/2000 | Blechman et al. |
| 6,178,353 B1 | 1/2001 | Griffith et al. |
| 6,190,305 B1 | 2/2001 | Ball et al. |
| 6,217,508 B1 | 4/2001 | Ball et al. |
| 6,227,820 B1 | 5/2001 | Jarvik |
| 6,292,678 B1 | 9/2001 | Hall et al. |
| 6,348,070 B1 | 2/2002 | Teissl et al. |
| 6,358,281 B1 | 3/2002 | Berrang et al. |
| 6,461,288 B1 | 10/2002 | Holcomb |
| 6,599,321 B2 | 7/2003 | Hyde, Jr. |
| 6,838,963 B2 | 1/2005 | Zimmerling |
| 7,091,806 B2 | 8/2006 | Zimmerling et al. |
| 7,190,247 B2 | 3/2007 | Zimmerling |
| 7,566,296 B2 | 7/2009 | Zimmerling et al. |
| 7,609,061 B2 | 10/2009 | Hochmair |
| 7,642,887 B2 | 1/2010 | Zimmerling |
| 7,680,525 B1 | 3/2010 | Damadian |
| 7,774,069 B2 | 8/2010 | Olson et al. |
| 7,856,986 B2 | 12/2010 | Darley |
| 7,881,800 B2 | 2/2011 | Daly et al. |
| 7,976,453 B2 | 7/2011 | Zimmerling et al. |
| 8,013,699 B2 | 9/2011 | Zimmerling |
| 8,118,725 B2 | 2/2012 | Zimmerling et al. |
| 8,255,058 B2 | 8/2012 | Gibson et al. |
| 8,340,774 B2 | 12/2012 | Hochmair et al. |
| 8,634,909 B2 | 1/2014 | Zimmerling et al. |
| 8,733,494 B1 | 5/2014 | Leigh |
| 8,734,475 B2 | 5/2014 | Ekvall et al. |
| 8,744,106 B2 | 6/2014 | Ball |
| 8,758,394 B2 | 6/2014 | Zimmerling et al. |
| 8,787,608 B2 | 7/2014 | Van Himbeeck et al. |
| 8,790,409 B2 | 7/2014 | Van den Heuvel et al. |
| 8,825,171 B1 | 9/2014 | Thenuwara et al. |
| 8,891,795 B2 | 11/2014 | Andersson |
| 8,897,475 B2 | 11/2014 | Ball et al. |
| RE45,701 E | 9/2015 | Zimmerling et al. |
| 9,126,010 B2 | 9/2015 | Shah et al. |
| 9,162,054 B2 | 10/2015 | Dalton |
| 9,227,064 B2 | 1/2016 | Duftner |
| 9,295,425 B2 | 3/2016 | Ball |
| 9,314,625 B2 | 4/2016 | Kasic, II et al. |
| 9,352,149 B2 | 5/2016 | Thenuwara et al. |
| RE46,057 E | 7/2016 | Zimmerling et al. |
| 9,392,382 B2 | 7/2016 | Nagl et al. |
| 9,420,388 B2 | 8/2016 | Ball |
| 9,549,267 B2 | 1/2017 | Nagl et al. |
| 9,615,181 B2 | 4/2017 | Nagl et al. |
| 9,656,065 B2 | 5/2017 | Tourrel et al. |
| 9,919,154 B2 | 3/2018 | Lee |
| 9,931,501 B2 | 4/2018 | Smyth |
| 10,300,276 B2 | 5/2019 | Lee et al. |
| 10,463,849 B2 | 11/2019 | Lee et al. |
| 10,532,209 B2 | 1/2020 | Lee et al. |
| 10,646,712 B2 | 5/2020 | Smith et al. |
| 10,646,718 B2 | 5/2020 | Smith et al. |
| 10,806,936 B2 | 10/2020 | Crawford et al. |
| 10,821,279 B2 | 11/2020 | Lee et al. |
| 2004/0012470 A1 | 1/2004 | Zimmerling et al. |
| 2004/0059423 A1 | 3/2004 | Barnes et al. |
| 2004/0063072 A1 | 4/2004 | Honkura et al. |
| 2004/0210103 A1 | 10/2004 | Westerkull |
| 2004/0260362 A1 | 12/2004 | Darley |
| 2005/0001703 A1 | 1/2005 | Zimmerling |
| 2005/0004629 A1* | 1/2005 | Gibson .................. A61N 1/375 607/60 |
| 2005/0062567 A1 | 3/2005 | Zimmerling et al. |
| 2006/0116743 A1 | 6/2006 | Gibson et al. |
| 2006/0244560 A1 | 11/2006 | Zimmerling et al. |
| 2007/0053536 A1 | 3/2007 | Westerkull |
| 2007/0126540 A1 | 6/2007 | Zimmerling |
| 2008/0097496 A1 | 4/2008 | Chang et al. |
| 2008/0103350 A1 | 5/2008 | Farone |
| 2008/0195178 A1 | 8/2008 | Kuzma |
| 2009/0048580 A1 | 2/2009 | Gibson |
| 2009/0099403 A1 | 4/2009 | Zimmerling et al. |
| 2009/0134721 A1 | 5/2009 | Zimmerling |
| 2009/0248155 A1 | 10/2009 | Parker |
| 2009/0287278 A1 | 11/2009 | Charvin |
| 2010/0004716 A1 | 1/2010 | Zimmerling et al. |
| 2010/0046778 A1 | 2/2010 | Crawford et al. |
| 2010/0046779 A1 | 2/2010 | Crawford et al. |
| 2011/0009925 A1 | 1/2011 | Leigh et al. |
| 2011/0022120 A1 | 1/2011 | Ball et al. |
| 2011/0068885 A1 | 3/2011 | Fullerton et al. |
| 2011/0218605 A1 | 9/2011 | Cryer |
| 2011/0224756 A1 | 9/2011 | Zimmerling et al. |
| 2011/0255731 A1 | 10/2011 | Ball |
| 2011/0264172 A1 | 10/2011 | Zimmerling et al. |
| 2012/0296155 A1 | 11/2012 | Ball |
| 2013/0079749 A1 | 3/2013 | Overstreet et al. |
| 2013/0150657 A1 | 6/2013 | Leigh et al. |
| 2013/0184804 A1 | 7/2013 | Dalton |
| 2013/0281764 A1 | 10/2013 | Bjorn et al. |
| 2013/0343588 A1 | 12/2013 | Karunasiri |
| 2014/0012069 A1 | 1/2014 | Ball |
| 2014/0012070 A1 | 1/2014 | Nagl et al. |
| 2014/0012071 A1 | 1/2014 | Nagl et al. |
| 2014/0012349 A1 | 1/2014 | Zimmerling |
| 2014/0121449 A1 | 5/2014 | Kasic et al. |
| 2014/0121586 A1 | 5/2014 | Bertrand et al. |
| 2014/0163692 A1 | 6/2014 | Van den Heuvel et al. |
| 2014/0336447 A1 | 11/2014 | Bjorn et al. |
| 2014/0343626 A1* | 11/2014 | Thenuwara ........ A61N 1/37229 607/57 |
| 2015/0025613 A1 | 1/2015 | Nyberg, II et al. |
| 2015/0073205 A1 | 3/2015 | Ball et al. |
| 2015/0087892 A1 | 3/2015 | Tourrel et al. |
| 2015/0094521 A1 | 4/2015 | Neuman et al. |
| 2015/0100109 A1 | 4/2015 | Feldman et al. |
| 2015/0265842 A1 | 9/2015 | Ridker |
| 2015/0320523 A1 | 11/2015 | Way et al. |
| 2015/0367126 A1 | 12/2015 | Smyth |
| 2015/0382114 A1 | 12/2015 | Andersson et al. |
| 2016/0008596 A1 | 1/2016 | Gibson et al. |
| 2016/0037273 A1 | 2/2016 | Gustafsson |
| 2016/0144170 A1 | 5/2016 | Gibson et al. |
| 2016/0205484 A1 | 7/2016 | Nagl et al. |
| 2016/0213936 A1 | 7/2016 | Heerlein et al. |
| 2016/0310737 A1 | 10/2016 | Tourrel et al. |
| 2016/0361537 A1 | 12/2016 | Leigh et al. |
| 2016/0381473 A1 | 12/2016 | Gustafsson |
| 2016/0381474 A1 | 12/2016 | Gustafsson et al. |
| 2017/0050027 A1 | 2/2017 | Andersson et al. |
| 2017/0078808 A1 | 3/2017 | Kennes |
| 2017/0156010 A1 | 6/2017 | Verma et al. |
| 2017/0239476 A1 | 8/2017 | Lee et al. |
| 2018/0028818 A1 | 2/2018 | Anderson et al. |
| 2018/0056084 A1 | 3/2018 | Alam |
| 2018/0110985 A1 | 4/2018 | Walter |
| 2018/0110986 A1 | 4/2018 | Lee |

(56) References Cited

U.S. PATENT DOCUMENTS

| | | | |
|---|---|---|---|
| 2018/0133486 A1 | 5/2018 | Smith | |
| 2018/0146308 A1* | 5/2018 | Leigh | H04R 25/60 |
| 2018/0160241 A1 | 6/2018 | Gustafsson et al. | |
| 2018/0160242 A1 | 6/2018 | Sriskandarajah | |
| 2018/0185634 A1 | 7/2018 | Smyth | |
| 2018/0249262 A1 | 8/2018 | Santek | |
| 2018/0270591 A1 | 9/2018 | Kennes | |
| 2018/0296826 A1 | 10/2018 | Lee et al. | |
| 2018/0303602 A1 | 10/2018 | Leigh | |
| 2018/0304078 A1 | 10/2018 | Crawford et al. | |
| 2018/0369586 A1 | 12/2018 | Lee et al. | |
| 2019/0015662 A1 | 1/2019 | Raje et al. | |
| 2019/0046797 A1 | 2/2019 | Calixto et al. | |
| 2019/0053908 A1 | 2/2019 | Cook et al. | |
| 2019/0076649 A1 | 3/2019 | Lee et al. | |
| 2019/0255316 A1 | 8/2019 | Lee et al. | |
| 2019/0298417 A1 | 10/2019 | Barrett et al. | |
| 2020/0114151 A1 | 4/2020 | Smith et al. | |
| 2020/0230422 A1 | 7/2020 | Gibson et al. | |
| 2020/0238088 A1 | 7/2020 | Smith et al. | |
| 2020/0330777 A1 | 10/2020 | Smith et al. | |
| 2020/0391023 A1 | 12/2020 | Lee et al. | |
| 2021/0046311 A1 | 2/2021 | Brehm et al. | |

FOREIGN PATENT DOCUMENTS

| | | |
|---|---|---|
| EP | 2560730 B1 | 11/2016 |
| EP | 3138605 A1 | 3/2017 |
| EP | 2098198 B1 | 9/2017 |
| WO | WO9858990 A1 | 12/1998 |
| WO | WO03081976 A2 | 10/2003 |
| WO | WO03092326 A1 | 11/2003 |
| WO | WO2004014269 A1 | 2/2004 |
| WO | WO2004014270 A1 | 2/2004 |
| WO | WO2007024657 A2 | 3/2007 |
| WO | WO2009124045 A1 | 10/2009 |
| WO | WO2009124174 A2 | 10/2009 |
| WO | WO2009149069 A2 | 12/2009 |
| WO | WO2010000027 A1 | 1/2010 |
| WO | WO2010083554 A1 | 7/2010 |
| WO | WO2011011409 A1 | 1/2011 |
| WO | WO2011109486 A2 | 9/2011 |
| WO | WO2011133747 A1 | 10/2011 |
| WO | WO2013043176 A1 | 3/2013 |
| WO | WO2013063355 A1 | 5/2013 |
| WO | WO2014011441 A1 | 1/2014 |
| WO | WO2014011582 A2 | 1/2014 |
| WO | WO2014046662 A1 | 3/2014 |
| WO | WO2014164023 A1 | 10/2014 |
| WO | WO2015065442 A1 | 5/2015 |
| WO | WO2016016821 A1 | 2/2016 |
| WO | WO2016190886 A1 | 12/2016 |
| WO | WO2016191429 A1 | 12/2016 |
| WO | WO2016207856 A1 | 12/2016 |
| WO | WO2017027045 A1 | 2/2017 |
| WO | WO2017027046 A1 | 2/2017 |
| WO | WO2017029615 A1 | 2/2017 |
| WO | WO2017034530 A1 | 3/2017 |
| WO | WO2017046650 A1 | 3/2017 |
| WO | WO2017087004 A1 | 5/2017 |
| WO | WO2017105510 A1 | 6/2017 |
| WO | WO2017105511 A1 | 6/2017 |
| WO | WO2017105604 A1 | 6/2017 |
| WO | WO2017172566 A1 | 10/2017 |
| WO | WO2018190813 A1 | 10/2018 |
| WO | WO2018191314 A1 | 10/2018 |
| WO | WO2018199936 A1 | 11/2018 |
| WO | WO2018217187 A1 | 11/2018 |
| WO | WO2019083540 A1 | 5/2019 |
| WO | WO2019160555 A1 | 8/2019 |
| WO | WO2020092185 A1 | 5/2020 |

OTHER PUBLICATIONS

Ju Hyun Jeon et al., "Reversing the Polarity of a Cochlear Implant Magnet After Magnetic Resonance Imaging," Auris Nasus Larynx, vol. 39, No. 4, pp. 415-417, Aug. 1, 2012.

Teissl et al., "Magentic Resonance Imaging and Cochlear Implants: Compatibility and Safety Aspects," Journal of Magnetic Resonance Imaging, Society For Magnetic Resonance Imaging, vol. 9, No. 1, pp. 26-38, Jan. 1, 1999.

U.S. Appl. No. 15/568,469, filed Oct. 21, 2017, 20180110985 A1.

U.S. Appl. No. 15/770,207, filed Apr. 22, 2018, U.S. Pat. No. 10,806,936.

U.S. Appl. No. 17/073,322, filed Oct. 17, 2020.

U.S. Appl. No. 16/060,383, filed Jun. 7, 2018, U.S. Pat. No. 10,532,209.

U.S. Appl. No. 15/591,054, filed May 9, 2017, U.S. Pat. No. 9,919,154.

U.S. Appl. No. 16/009,600, filed Jun. 15, 2018, U.S. Pat. No. 10,821,279.

U.S. Appl. No. 16/403,582, filed May 5, 2019, U.S. Pat. No. 10,463,849.

U.S. Appl. No. 17/008,291, filed Aug. 31, 2020, 20200391023 A1.

U.S. Appl. No. 16/610,502, filed Nov. 2, 2019.

U.S. Appl. No. 15/568,470, filed Oct. 21, 2017, U.S. Pat. No. 10,300,276.

U.S. Appl. No. 16/101,390, filed Aug. 10, 2018, 20190046797 A1.

U.S. Appl. No. 15/703,808, filed Sep. 13, 2017, U.S. Pat. No. 10,646,712.

U.S. Appl. No. 15/805,025, filed Nov. 6, 2017, U.S. Pat. No. 10,646,718.

U.S. Appl. No. 16/852,457, filed Apr. 18, 2020, 20200238088 A1.

U.S. Appl. No. 16/499,311, filed Sep. 29, 2019.

U.S. Appl. No. 16/603,868, filed Oct. 9, 2019, 20200114151 A1.

U.S. Appl. No. 16/754,126, filed Apr. 6, 2020, 20200330777 A1.

U.S. Appl. No. 16/966,885, filed Aug. 1, 2020, 20210046311 A1.

* cited by examiner

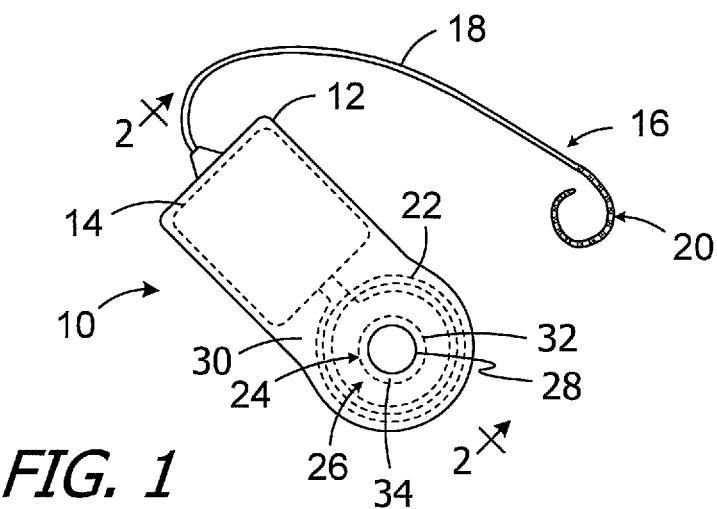
FIG. 1
Prior Art
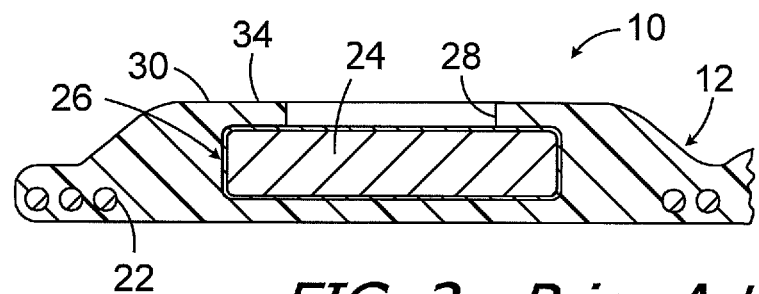
FIG. 2 - Prior Art
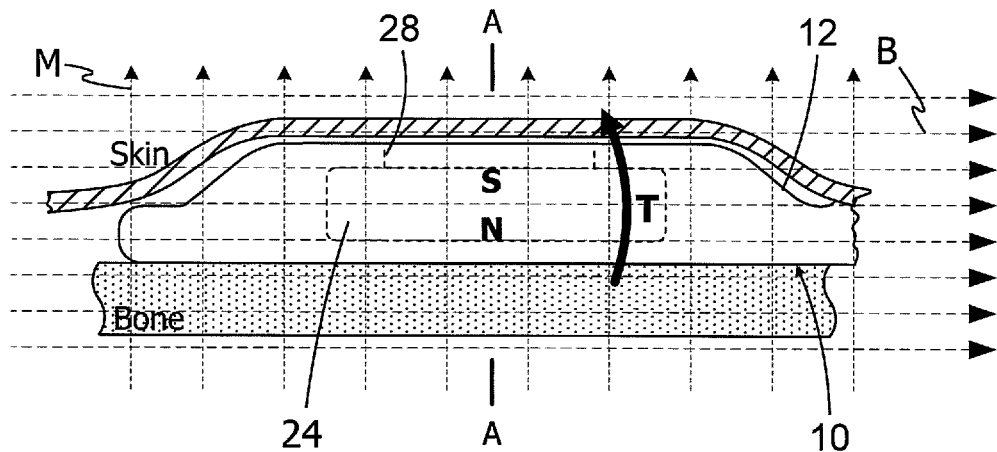
FIG. 3 - Prior Art

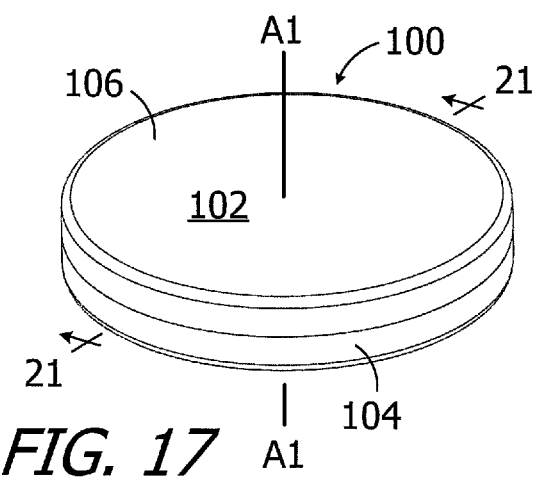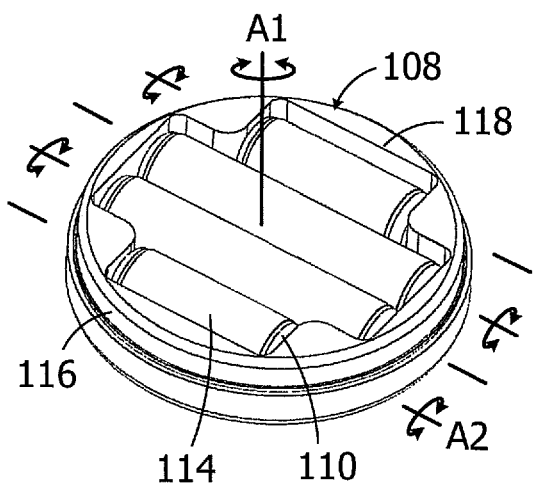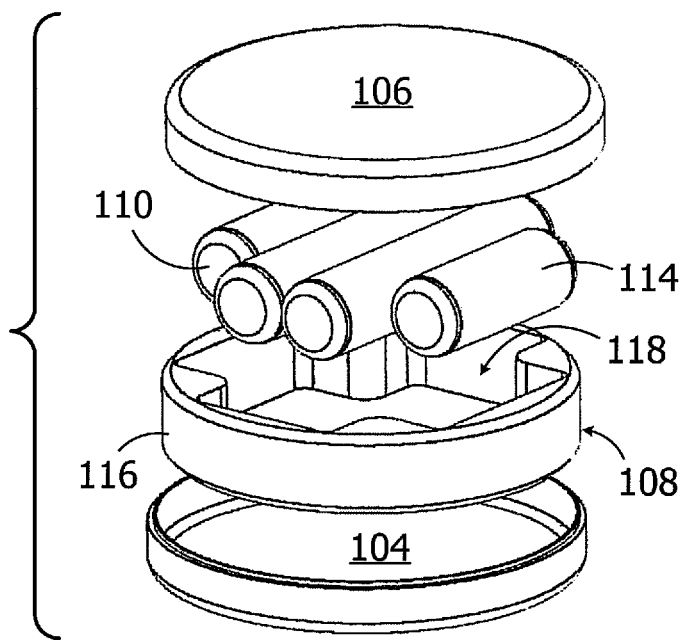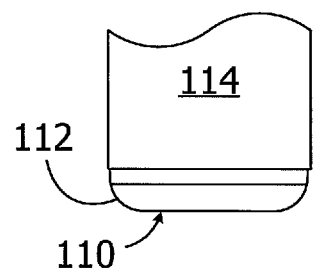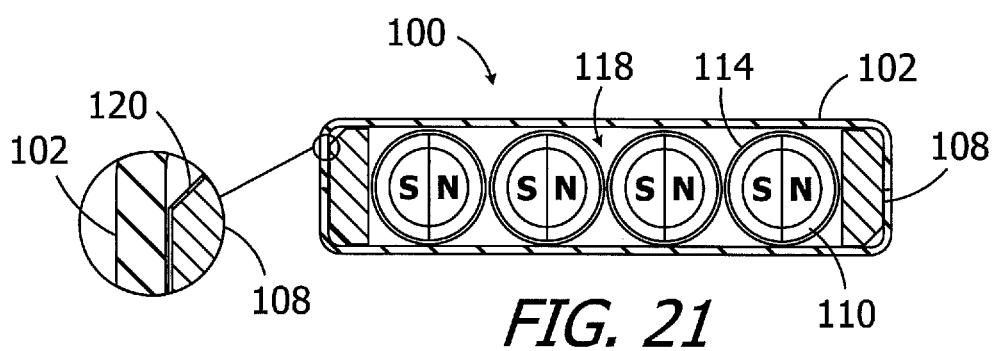

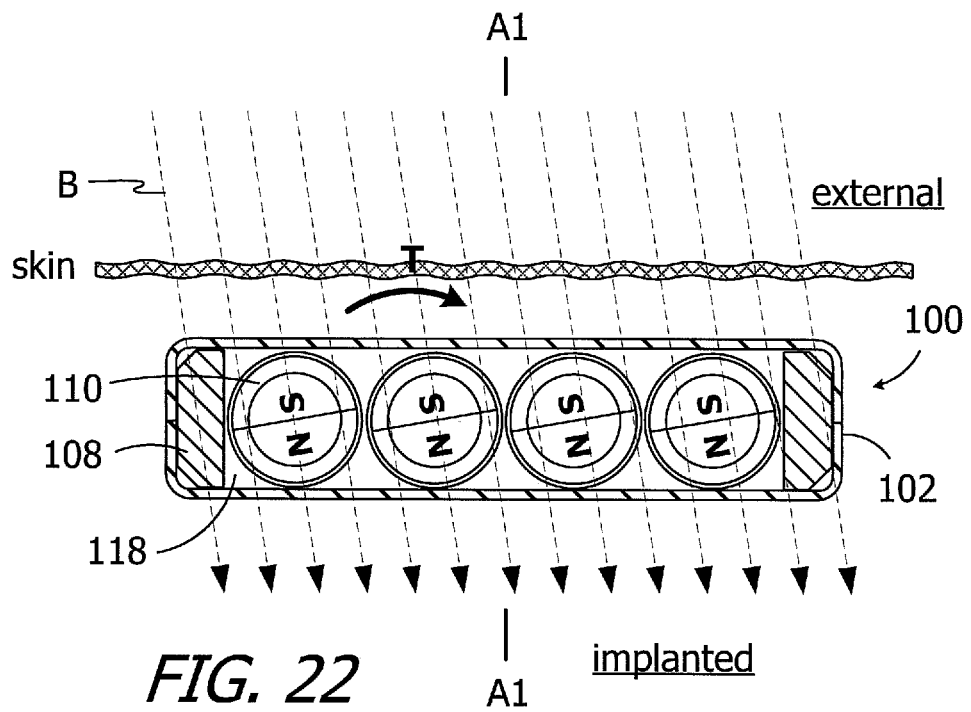
FIG. 22
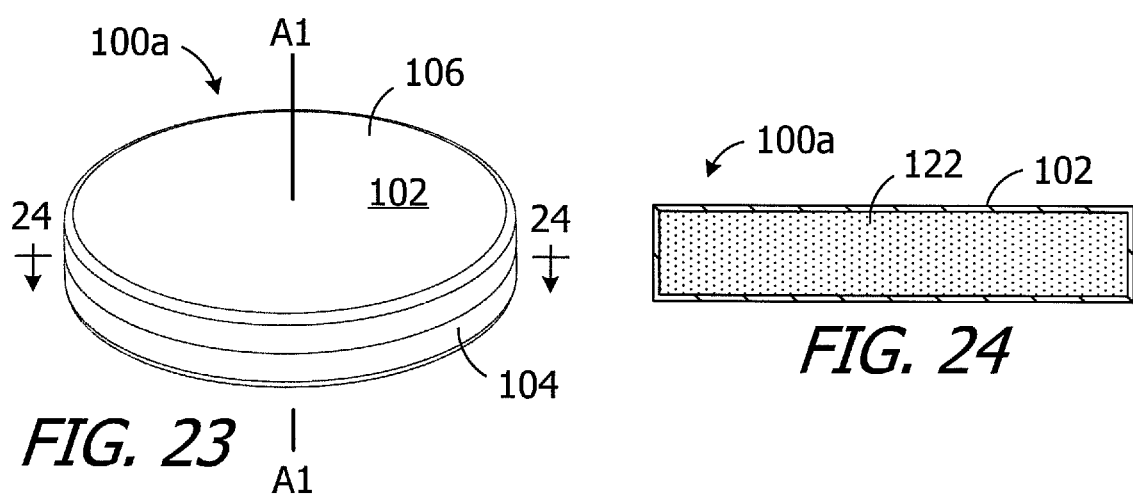
FIG. 23
FIG. 24

COCHLEAR IMPLANTS, MAGNETS FOR USE WITH SAME AND MAGNET RETROFIT METHODS

CROSS-REFERENCE TO RELATED APPLICATIONS

This application is the U.S. National Stage of PCT App. Ser. No. PCT/US2018/026978, filed Apr. 10, 2018, which is a continuation-in-part of PCT App. Ser. No. PCT/US2017/027041, filed Apr. 11, 2017.

BACKGROUND

1. Field

The present disclosure relates generally to the implantable portion of implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths, rates and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Harmony™ BTE sound processor, the Naida™ CI Q Series sound processor and the Neptune™ body worn sound processor, which are available from Advanced Bionics.

As alluded to above, some ICS systems include an implantable cochlear stimulator (or "cochlear implant"), a sound processor unit (e.g., a body worn processor or behind-the-ear processor), and a microphone that is part of, or is in communication with, the sound processor unit. The cochlear implant communicates with the sound processor unit and, some ICS systems include a headpiece that is in communication with both the sound processor unit and the cochlear implant. The headpiece communicates with the cochlear implant by way of a transmitter (e.g., an antenna) on the headpiece and a receiver (e.g., an antenna) on the implant. Optimum communication is achieved when the transmitter and the receiver are aligned with one another. To that end, the headpiece and the cochlear implant may include respective positioning magnets that are attracted to one another, and that maintain the position of the headpiece transmitter over the implant receiver. The implant magnet may, for example, be located within a pocket in the cochlear implant housing.

One example of a conventional cochlear implant (or "implantable cochlear stimulator") is the cochlear implant 10 illustrated in FIGS. 1 and 2. The cochlear implant 10 includes a flexible housing 12 formed from a silicone elastomer or other suitable material (e.g., with a hardness from 50 to 70 Shore A), a processor assembly 14, a cochlear lead 16 with a flexible body 18 and an electrode array 20, and an antenna 22 that may be used to receive data and power by way of an external antenna that is associated with, for example, a sound processor unit. The antenna 22 is located within an antenna portion 23 of the housing 12. A cylindrical positioning magnet 24, with north and south magnetic dipoles that are aligned in the axial direction of the disk, is located within the housing 12. The positioning magnet 24 is used to maintain the position of a headpiece transmitter over the antenna 22.

There are some instances where it is necessary to remove the magnet from a conventional cochlear implant, and then reinsert the magnet, in situ, i.e., with the cochlear implant accessed by way of an incision in the skin. To that end, the positioning magnet 24 is carried within an internal magnet pocket 26 and can be inserted into, and removed from, the housing pocket by way of a magnet aperture 28 that extends through the housing top wall 30. The magnet 22 is larger than the magnet aperture 28, i.e., the outer perimeter of the magnet is greater than the perimeter of the magnet aperture. The portion of the top wall 30 between the aperture 28 and the outer edge 32 of the magnet 24 forms a retainer 34 that, absent deformation of the aperture and retainer, prevents the magnet from coming out of the housing 12. During installation and removal, the aperture 28 and retainer 34 are stretched or otherwise deformed so that the magnet 24 can pass through the aperture 28.

The present inventor has determined that conventional cochlear implants are susceptible to improvement. For example, removal and reinsertion of the implant magnet by way of the aperture may be required because some conventional cochlear implants are not compatible with magnetic resonance imaging ("MRI") systems. As illustrated in FIG. 3, the implant positioning magnet 24 produces a magnetic field M in a direction that is perpendicular to the patient's skin and parallel to the axis A. This magnetic field direction is not aligned with, and may be perpendicular to (as shown), the direction of the MRI magnetic field B. The misalignment of the interacting magnetic fields M and B is problematic for a number of reasons. The dominant MRI magnetic field B (typically 1.5 Tesla or more) may generate a significant amount of torque T on the implant magnet 24. The torque T may be sufficient to deform the retainer 34, dislodge the implant magnet 24 from the pocket 26, and cause reorientation of the implant magnet. Reorientation of the magnet 24 can place significant stress on the dermis (or "skin"), which cause significant pain. In some instances, the implant magnet 24 may rotate 180 degrees, thereby reversing the N-S orientation of the magnet.

As alluded to above, magnet rotation may be avoided by surgically removing the positioning magnet prior to the MRI procedure and then reinserting the magnet after the procedure. A wide variety of removable positioning magnets, and removable positioning magnet systems, have been employed in conventional cochlear implants. The manner in which the magnet is removed from the magnet pocket will depend upon the type of magnet or magnet system. For example, some positioning magnets simply include magnetic material that is hermetically sealed within a biocompatible case (such as a titanium case) or magnetic material that is sealed within a biocompatible coating, and may be removed from the magnet pocket in the manner described above. Positioning magnet 24 is one example of a positioning magnet that includes magnet material within a titanium case. Other positioning magnets are part of systems that include structures which are capable preventing magnet reorientation in relatively low strength MRI magnetic fields. For example, U.S. Pat. No. 9,352,149 discloses a system that includes a retainer which surrounds the magnet pocket and is embedded within the implant housing and a magnet case that may be secured to the retainer through the use of threads (or other mechanical interconnects) on the retainer and magnet case. U.S. Pat. Pub. No. 2016/0144170 discloses an embedded retainer (referred to as a "mounting") and a magnet that include mechanical interconnects that allow the magnet to be rotated into engagement with the retainer, as well as other releasable mechanical connectors that secure the magnet within the magnet pocket and allow removal of the magnet as necessary. Other systems, such as those disclosed in U.S. Pat. No. 8,340,774, include a retainer in which the magnet is located. The retainer (in which the magnet is located) may be inserted into an opening in the elastomeric housing of the associated cochlear implant, and also removed from the housing if necessary. References herein to "positioning magnets" include all such removable positioning magnets as well as the removable magnetic portions of all such systems.

The present inventor has determined that removal and reinsertion can be problematic because some patients will have many MRI procedures during their lifetimes, and repeated surgeries can result in skin necrosis at the implant site. More recently, implant magnet apparatus that are compatible with MRI systems have been developed. Examples of MRI-compatible magnet apparatus are disclosed in WO2016/190886 and PCT App. Ser. No. PCT/US2016/056351 (WO2017/105604), which are incorporated herein by reference in their entireties. The present inventor has determined that although MRI-compatible magnet apparatus are an advance in the art, such magnet apparatus will not physically fit into the magnet pocket of many older cochlear implants that are already implanted in patients. Accordingly, the present inventor has determined that it would be desirable to provide apparatus and methods that facilitate the replacement of a conventional implant magnet with a MRI-compatible magnet apparatus, even in those instances where the MRI-compatible magnet apparatus will not physically fit into the magnet pocket of the associated cochlear implant.

SUMMARY

A cochlear implant exomagnet in accordance with at least one of the present inventions includes a magnet apparatus and a magnet mount configured to secure the magnet apparatus to a cochlear implant in such a manner that the magnet apparatus is not located within the internal magnet pocket of the cochlear implant.

A cochlear implant exomagnet in accordance with at least one of the present inventions includes a magnet apparatus and means for anchoring the magnet apparatus to the internal magnet pocket in such a manner that the magnet apparatus is not located within the internal magnet pocket.

The present inventions also include cochlear implants that include such exomagnets, systems with such cochlear implants in combination with a headpiece, and systems with such cochlear implants in combination with both a headpiece and a sound processor.

A method in accordance with at least one of the present inventions includes the steps of removing an implant magnet from a magnet pocket of a cochlear implant housing and replacing the implant magnet with a magnet apparatus that is anchored to, but is not located within, the magnet pocket.

A method in accordance with at least one of the present inventions includes the steps of disconnecting a magnet apparatus from an anchor that occupies the entire magnet pocket of a cochlear implant housing that is located within a patient, and removing the disconnected magnet apparatus from the patient.

There are a number of advantages associated with such apparatus and systems. For example, exomagnets may be provided with a variety of magnet mount configurations that respectively conform to a variety of magnet pocket configurations, thereby allowing the replacement of a conventional implant magnet with an MRI-compatible magnet apparatus that may not physically fit into the magnet pocket of the associated cochlear implant, and eliminating the need for multiple magnet removal and reinsertion surgeries should multiple MRI procedures be required during a patient's lifetime.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 1 is a plan view of a conventional cochlear implant.

FIG. 2 is a section view taken along line 2-2 in FIG. 1.

FIG. 3 is a section view showing the conventional cochlear implant as an MRI magnetic field is being applied.

FIG. 12 is a side view of a portion of the cochlear implant illustrated in

FIG. 11.

FIG. 15 is a bottom view of the cochlear implant exomagnet illustrated in

FIG. 4.

FIG. 17 is a perspective view of an implant magnet apparatus in accordance with one embodiment of a present invention.

FIG. 18 is a perspective view of a portion of the implant magnet apparatus illustrated in FIG. 17.

FIG. 19 is an exploded view of the implant magnet apparatus illustrated in FIG. 17.

FIG. 20 is a plan view of a portion of the implant magnet apparatus illustrated in FIG. 17.

FIG. 21 is a section view take along line 21-21 in FIG. 17.

FIG. 22 is a section view similar to FIG. 21 with the implant magnet apparatus in an MRI magnetic field.

FIG. 23 is a perspective view of an implant magnet apparatus in accordance with one embodiment of a present invention.

FIG. 24 is a section view take along line 24-24 in FIG. 23.

DETAILED DESCRIPTION OF THE EXEMPLARY EMBODIMENTS

Figure 4:
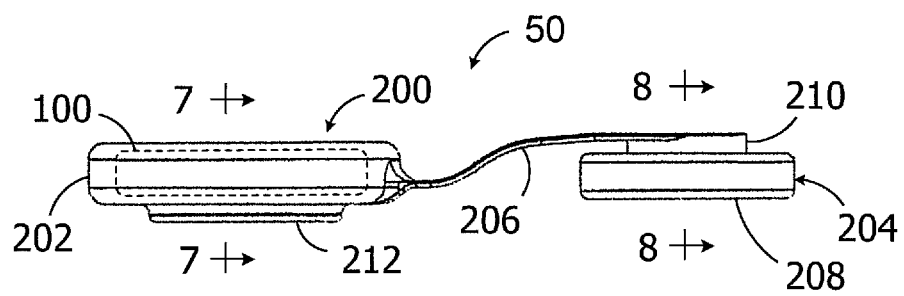
FIG. 4 is a side view of a cochlear implant exomagnet in accordance with one embodiment of a present invention.
Figure 5:
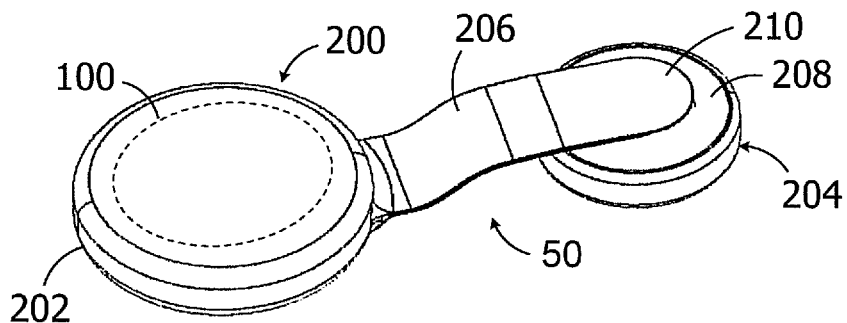
FIG. 5 is a top perspective view of the cochlear implant exomagnet illustrated in FIG. 4.
Figure 6:
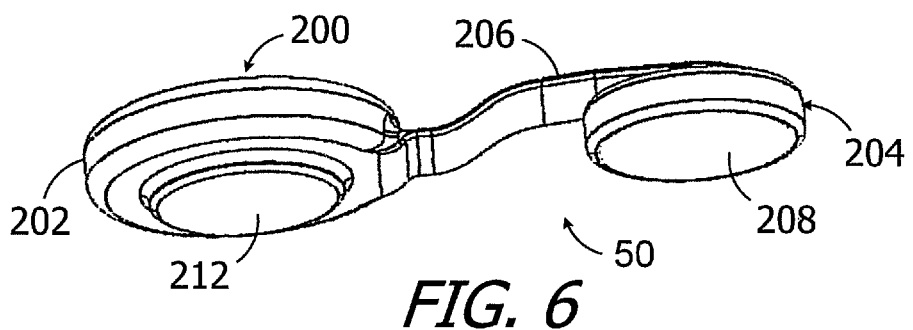
FIG. 6 is a bottom perspective view of the cochlear implant exomagnet illustrated in FIG. 4.
Figure 7:
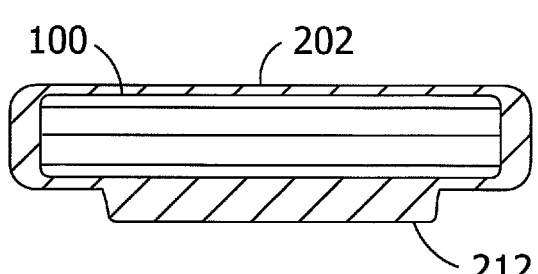
FIG. 7 is a partial section view taken along line 7-7 in FIG. 4.
Figure 8:
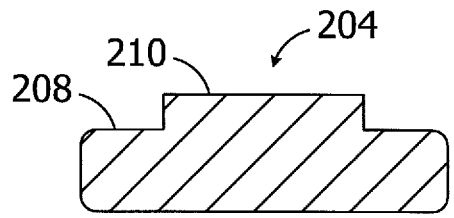
FIG. 8 is a section view taken along line 8-8 in FIG. 4.

The following is a detailed description of the best presently known modes of carrying out the inventions. This description is not to be taken in a limiting sense, but is made merely for the purpose of illustrating the general principles of the inventions.

One example of a cochlear implant exomagnet, which is generally represented by reference numeral 50, is illustrated in FIGS. 4-8. An "exomagnet" is a device that can be secured to a cochlear implant to position a magnet or a magnet apparatus (e.g., a MRI-compatible magnet apparatus) outside of the internal magnet pocket of the associate cochlear implant. The exemplary exomagnet 50 includes a positioning magnet apparatus 100 ("or magnet apparatus") and a magnet mount 200 that may be used to secure the magnet apparatus to a cochlear implant from which the conventional implant magnet has been removed in the manner described below with reference to FIGS. 9-12.

The exemplary magnet apparatus 100, which is discussed in greater detail below with reference to FIGS. 17-22, is used to retain a headpiece over the associated cochlear implant. The exemplary magnet mount 200 includes a housing 202 for the magnet apparatus 100, an anchor 204 that is configured to be inserted into the internal magnet pocket of the associated cochlear implant, and connector 206 that extends from the housing to the anchor. The exemplary housing 202 is a disk-shaped structure in which the magnet apparatus 100 is located. The exemplary anchor 204 includes a relatively wide portion 208 that is sized and shaped in a manner corresponding to the magnet pocket of the associated cochlear implant, and a relatively narrow portion 210 that is sized and shaped to extend through the magnet aperture of the associated cochlear implant. By way of example, but not limitation, the diameter of the relatively wide portion 208 may range from 9 mm to 16 mm and the thickness may range from 1.5 mm to 3.0 mm, depending on the size of the associated magnet pocket, as may the other relatively wide portions described below. The exemplary connector 206 is a thin, flexible strap that extends from the housing 202 to the relatively narrow portion 210 of the anchor 204. A pedestal 212 may be located on the bottom surface of the housing 202. The pedestal 212 may be used to position the magnet apparatus 100 closer to the external headpiece magnet. Alternatively, an indentation (or "well") may be formed in the bone at the desired magnet apparatus location, and the pedestal 212 may be positioned in the indentation to prevent post-surgical movement.

The magnet mount 200 may, in some instances, be a molded structure that encases the magnet apparatus 100 formed from silicone elastomers or other suitable non-magnetic materials. As such, the non-magnetic anchor 204 will replace a conventional implant magnet in the magnet pocket. The anchor 204, and in some instances the entire magnet mount 200, may also be formed from a material that is harder than the housing material of the associated cochlear implant (e.g., silicone with a hardness from 80 to 90 Shore A as compared to an exemplary implant housing hardness of 50 to 70 Shore A) to facilitate insertion of the anchor into the magnet pocket in a manner similar to a conventional implant magnet. In other instances, a rigid magnet mount may be formed from, for example, injection molded material such as PEEK.

Figure 9:
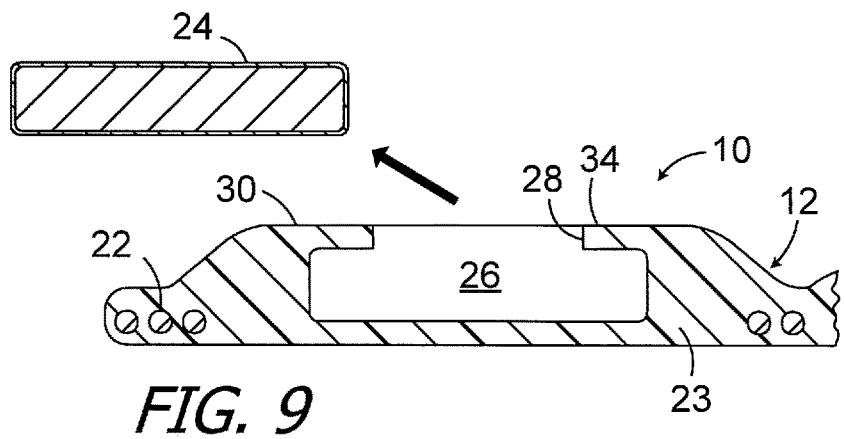
FIG. 9 is a section view showing a step in a method in accordance with one embodiment of a present invention.
Figure 10:
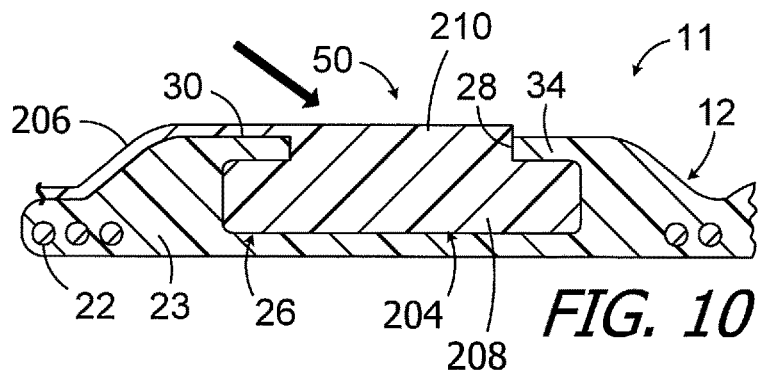
FIG. 10 is a section view showing a step in a method in accordance with one embodiment of a present invention.
Figure 11:
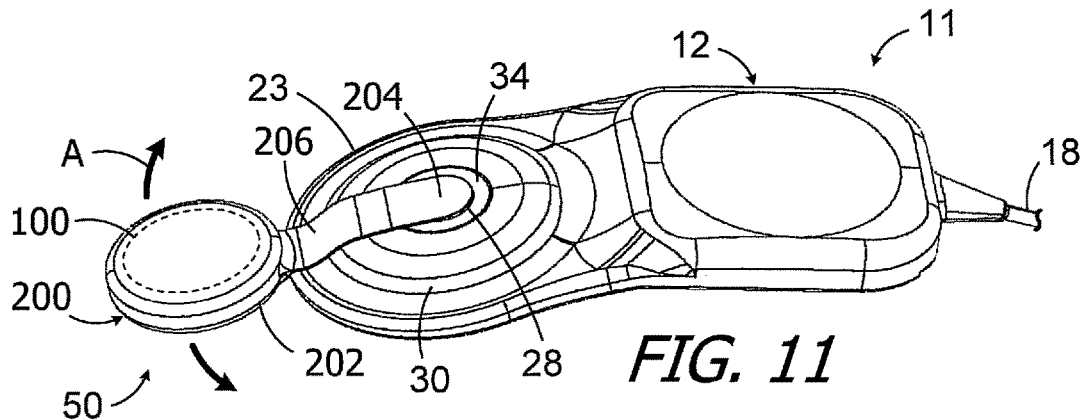
FIG. 11 is a perspective view of a cochlear implant including the exomagnet illustrated in FIG. 4.
Figure 12:
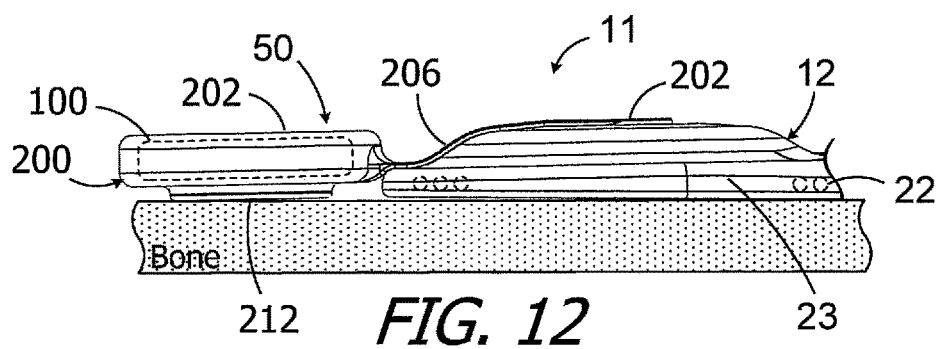

One example of a retrofit method involving the exemplary exomagnet 50 is illustrated in FIGS. 9 and 10, and the resulting cochlear implant 11 is illustrated in FIGS. 11 and 12. The cochlear implant 11 is identical to the cochlear implant 10 but for the fact that the cochlear includes the exomagnet 50 instead of the positioning magnet 24. The exemplary retrofit method involves removing the positioning magnet 24 from cochlear implant 10 and replacing the positioning magnet 24 with the exomagnet 50 in situ, i.e., with the cochlear implant accessed by way of an incision in the skin (not shown). To that end, and referring first to FIG. 9, the positioning magnet 24 may be removed from the internal magnet pocket 26 by way of the magnet aperture 28. The positioning magnet 24 may also be removed from the user's head by way of the incision.

Next, as illustrated in FIG. 10, the anchor 204 of the exemplary exomagnet 50 may be inserted into the internal magnet pocket 26 by way of a magnet aperture 28 to connect exomagnet the housing 12. The relatively wide portion 208 has, in the exemplary implementation, the same size and shape as the positioning magnet 24. The flexible connector 206 may conform to the shape of the implant housing top wall 30 (as shown), and the length of the flexible connector is such that the magnet mount 200 and the magnet apparatus 100 are located beyond, but adjacent to, the antenna portion 23 of the housing 12. Put another way, and referring to FIG. 12, the magnet apparatus 100 is not located within the cochlear implant housing 12 in general and, more specifically, is not located with antenna portion 23 of the housing 12 and is not located within the perimeter defined by the antenna 22.

It should also be noted here that the respective shapes of the internal magnet pocket 26 and the exomagnet anchor 204 may be configured to allow the location of the exomagnet 50 to be varied relative to the cochlear implant housing 12. In the illustrated implementation, the magnet pocket 26 and the exomagnet anchor 204 are circular disk-shaped, which allows the exomagnet 50 to pivot in the directions identified by arrows A. For example, the exomagnet 50 may be pivotable up to 90 degrees in each direction. Such positioning allows the surgeon to position the exomagnet 50 in the most desirable location relative to the remainder of the implant 11, in view of anatomic considerations and used-based considerations such as sleeping position, eyeglass position, and desired headpiece location (as is discussed below with reference to FIG. 27).

Figure 13:
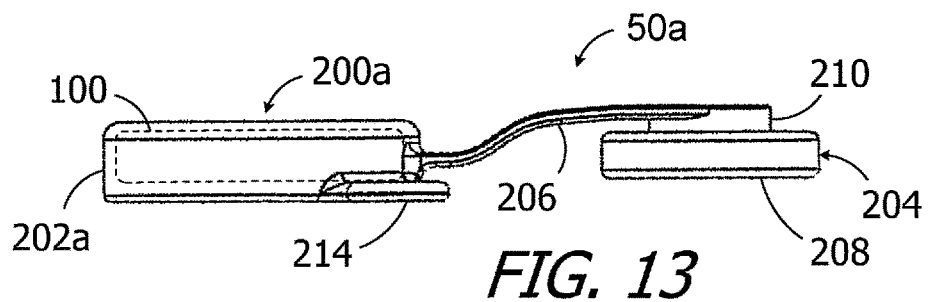
FIG. 13 is a side view of a cochlear implant exomagnet in accordance with one embodiment of a present invention.
Figure 14:
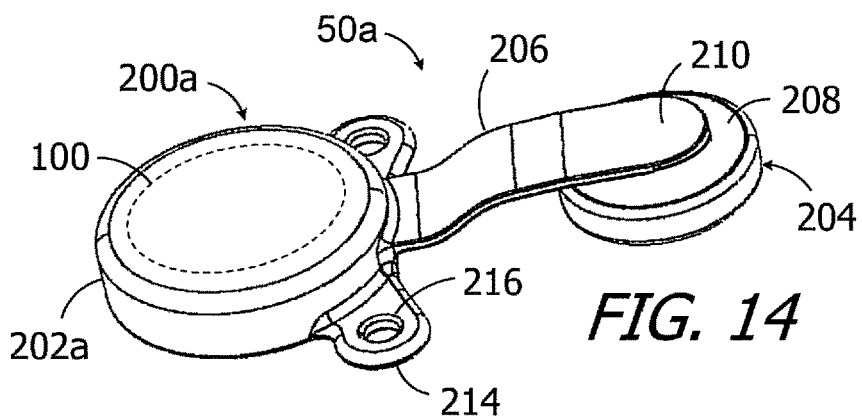
FIG. 14 is a top perspective view of the cochlear implant exomagnet illustrated in FIG. 13.
Figure 15:
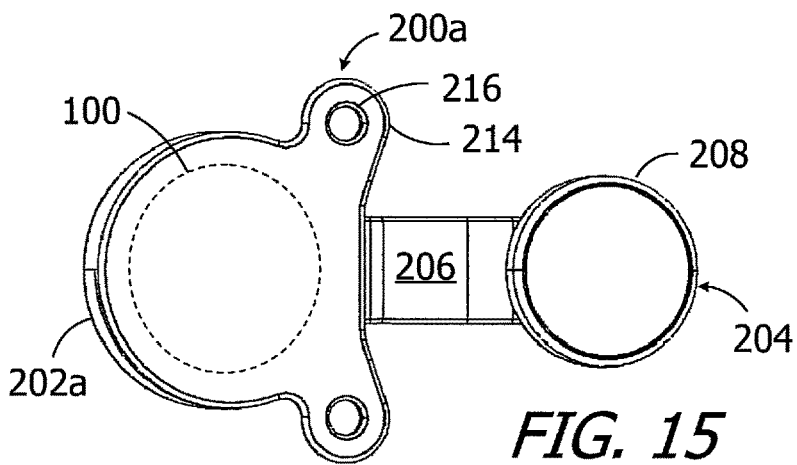
Figure 16:
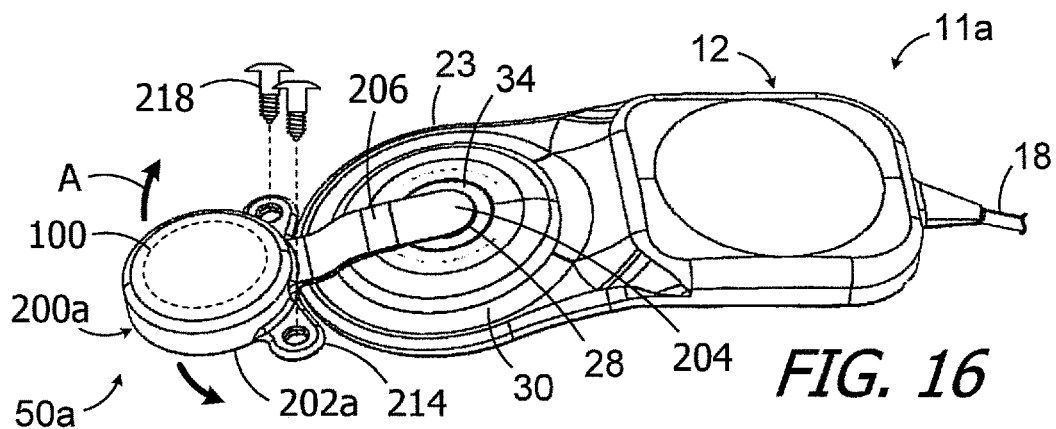
FIG. 16 is a perspective view of a cochlear implant including the exomagnet illustrated in FIG. 13.

Another exemplary exomagnet is generally represented by reference numeral 50*a* FIGS. 13-15. The exomagnet 50*a* is substantially similar to exomagnet 50 and similar elements are represented by similar reference numerals. The exemplary exomagnet 50*a* may be incorporated into a cochlear implant 11*a* in the manner illustrated in FIG. 16. Here, however, exomagnet is configured to be secured to the skull with bone screws in those instances where the surgeon anticipates that the either the exomagnet or the cochlear implant housing 12 could be susceptible to post-surgery migration. In particular, the exemplary exomagnet 50*a* includes a magnet mount 200*a* with a housing 202*a*. The housing 202*a* has a pair of tabs 214 with apertures 216. Bone screws 218 (e.g., standard bone screws and self-drilling bone screws) may be inserted through the apertures 216 and driven into the bone to secure each tab 214 to bone, thereby fixing the position of the exomagnet 50*a*, as shown in FIG. 16.

The magnet mounts 200 and 200*a* may be reconfigured (if necessary) to accommodate cochlear implants with magnet apertures that extend through the bottom surface of the housing instead of the top surface (as shown). Similarly, the magnet mounts 200 and 200*a* may be reconfigured (if necessary) to accommodate cochlear implants with magnet apertures that extend through both the top and bottom surfaces of the housing. For example, some cochlear implants include hourglass-shaped magnets and corresponding hourglass-shaped magnet pockets with openings that extend through the top and bottom surfaces. Here, an hourglass-shaped anchor (not shown) may be employed.

Other exomagnets (not shown) may be provided with anchors that are configured to mate with, or be otherwise held by, mechanical retainers such as, for example, those discussed above with reference to U.S. Pat. Nos. 9,352,149 and 8,340,774 and U.S. Pat. Pub. No. 2016/0144170.

Turning to FIGS. 17-21, the exemplary MRI-compatible magnet apparatus 100 includes a case 102, with a base 104 and a cover 106, a magnet frame 108, and a plurality of elongate diametrically magnetized magnets 110 within the frame that define a N-S direction. The exemplary case 102 is disk-shaped and defines a central axis A1, which is also the central axis of the magnet frame 108. The magnet frame 108 is freely rotatable relative to the case 102 about the central axis A1 over 360°. The magnets 110 rotate with the magnet frame 108 about the central axis A1. Each magnet 110 is also freely rotatable relative to the magnet frame 108 about its own longitudinal axis A2 over 360°. In the illustrated implementation, the longitudinal axes A2 are parallel to one another and are perpendicular to the central axis A1.

Given the ability of each magnet 110 to freely rotate about its longitudinal axis A2, the magnets 110 align with one another in the N-S direction in the absence of a relatively strong external magnetic field (e.g., the MRI magnetic field discussed below with reference to FIG. 22), and the at rest N-S orientation of the magnets 110 will be perpendicular to the central axis A1. So oriented, the magnetic fields of the diametrically magnetized magnets 110 are aligned with the magnetic field of a diametrically magnetized disk-shaped positioning magnet, such as a headpiece magnet 410 (discussed below with reference to FIGS. 25 and 26). It should also be noted here that the magnetic field of the positioning magnet will not be strong enough to cause the magnets 110 to rotate out of the illustrated at rest N-S orientation. Although the frame 108 will rotate as necessary, the magnets 110 will remain in the N-S orientation illustrated in FIG. 21 and will continue to function as a magnetic unit in the presence of a headpiece magnet.

The exemplary case 102 is not limited to any particular configuration, size or shape. In the illustrated implementation, the case 102 is a two-part structure that includes the base 104 and the cover 106 which are secured to one another in such a manner that a hermetic seal is formed between the cover and the base. Suitable techniques for securing the cover 106 to the base 104 include, for example, seam welding with a laser welder. With respect to materials, the case 102 may be formed from biocompatible paramagnetic metals, such as titanium or titanium alloys, and/or biocompatible non-magnetic plastics such as polyether ether ketone (PEEK), low-density polyethylene (LDPE), high-density polyethylene (HDPE), ultra-high-molecular-weight polyethylene (UHMWPE), polytetrafluoroethylene (PTFE) and polyimide. In particular, exemplary metals include commercially pure titanium (e.g., Grade 2) and the titanium alloy Ti-6Al-4V (Grade 5), while exemplary metal thicknesses may range from 0.20 mm to 0.25 mm. With respect to size and shape, the case 102 may have an overall size and shape similar to that of conventional cochlear implant magnets, although such sizing/shaping is not required because the magnet apparatus is not located within the cochlear implant housing 22.

Although the present inventions are not limited to any particular number, there are four elongate diametrically magnetized magnets 110 in the exemplary magnet apparatus 100. Two of the otherwise identical magnets 110 are relatively long and two are relatively short in order to efficiently utilize the available volume within the case 102. The exemplary magnets 110 are circular in a cross-section, have rounded corners 112, and are located within low friction tubes 114. Suitable materials for the magnets 110 include, but are not limited to, neodymium-boron-iron and samarium-cobalt.

The exemplary magnet frame 108 includes a disk 116 and a magnet receptacle 118 that extends completely through the disk. The magnet receptacle 118 is configured to hold all of the magnets 110 (four in the illustrated embodiment) and includes a relatively long portion and two relatively short portions. Suitable materials for the frame 108, which may be formed by machining or injection molding, include paramagnetic metals, polymers and plastics such as those discussed above in the context of the case 102.

The inner surfaces of the case 102 (and other cases discussed below) and/or the surfaces of the frame 108 may be coated with a lubricious layer. The lubricious layer may be in the form of a specific finish of the surface that reduces friction, as compared to an unfinished surface, or may be a coating of a lubricious material such as diamond-like carbon (DLC), titanium nitride (TiN), PTFE, polyethylene glycol (PEG), Parylene, fluorinated ethylene propylene (FEP) and electroless nickel sold under the tradenames Nedox® and Nedox PF™. The DLC coating, for example, may be only 0.5 to 5 microns thick. In those instances where the base 104 and a cover 106 are formed by stamping, the finishing process may occur prior to stamping. Micro-balls, biocompatible oils and lubricating powders may also be added to the interior of the case to reduce friction. In the illustrated implementation, the surfaces of the frame 108 may be coated with a lubricious layer 120 (e.g., DLC), while the inner surfaces of the case 102 do not include a lubricious layer. The lubricious layer 120 reduces friction between the case 102 and frame 108, while the low friction tubes 114 reduce friction between adjacent magnets 110 as well as between the case 102 and the magnets 110.

Turning to FIG. 22, when exposed to a dominant MRI magnetic field B, the torque T on the magnets 110 will rotate the magnets about their axis A2, thereby aligning the magnetic fields of the magnets 110 with the MRI magnetic field B. The magnet frame 108 will also rotate about axis A1 as necessary to align the magnetic fields of the magnets 110 with the MRI magnetic field B. When the magnet apparatus 100 is removed from the MRI magnetic field B, the magnetic attraction between the magnets 110 will cause the magnets to rotate about axis A2 back to the orientation illustrated in FIG. 21, where they are aligned with one another in the N-S direction and the N-S orientation of the magnets is perpendicular to the central axis A1 of the case 102.

Additional information concerning magnet apparatus 100 and other similar MRI-compatible magnet apparatus may be found in PCT App. Ser. No. PCT/US2016/056351 (WO2017/105604), which is incorporated herein by reference in its entirety.

Another exemplary MRI-compatible magnet apparatus is generally represented by reference numeral 100a in FIGS. 23 and 24. The magnet apparatus 100a includes a case 102, with base 104 and a cover 106, and magnetic material particles (or "particles") 108 within the internal volume of a case 102. The particles 122 are in contact with one another and are independently and freely rotatable and otherwise movable relative to one another and to the case. The particles 122 are free to move from one X-Y-Z coordinate to another and/or rotate in any direction. For example, some particles 122 may move linearly and/or rotate relative to other particles and relative to the case 102, while the orientation of the case remains the same, when the magnet apparatus 100a is exposed to an external magnetic field. Although the present magnetic material particles are not limited to any particular shape, the exemplary magnetic material particles 122 may be spherical or may be non-spherical, polyhedral shapes or at least substantially polyhedral shapes, i.e., multi-sided shapes that are regular or irregular, symmetric or asymmetric, with or without smooth side surfaces, and with or without straight edges, that will permit the particles to rotate relative to one another when loosely packed. Any three-dimensional shapes that permit the movement described above may also be employed. The magnetic material particles 122 may be formed from any suitable magnetic material. Such materials include, but are not limited to, neodymium-iron-boron ("$Nd_2Fe_{14}B$") magnetic material, isotropic neodymium, anisotropic neodymium, samarium-cobalt ("$Sm_2Co_{17}$"). Additional information concerning magnet apparatus 100a and other similar MRI-compatible magnet apparatus may be found in PCT Pat. Pub. No. WO2016/190886, which is incorporated herein by reference in its entirety.

It should be noted here that the present exomagnets are not limited to the MRI-compatible magnet apparatus described above or any other particular type of magnet apparatus. The magnet apparatus illustrated in U.S. Pat. No. 8,634,909, which has been proposed for use in a MRI magnetic field, is another example of a magnet apparatus that may be incorporated into the present exomagnets. Still other MRI-compatible magnet apparatuses are discussed below with reference to FIGS. 44-53.

Figure 25:
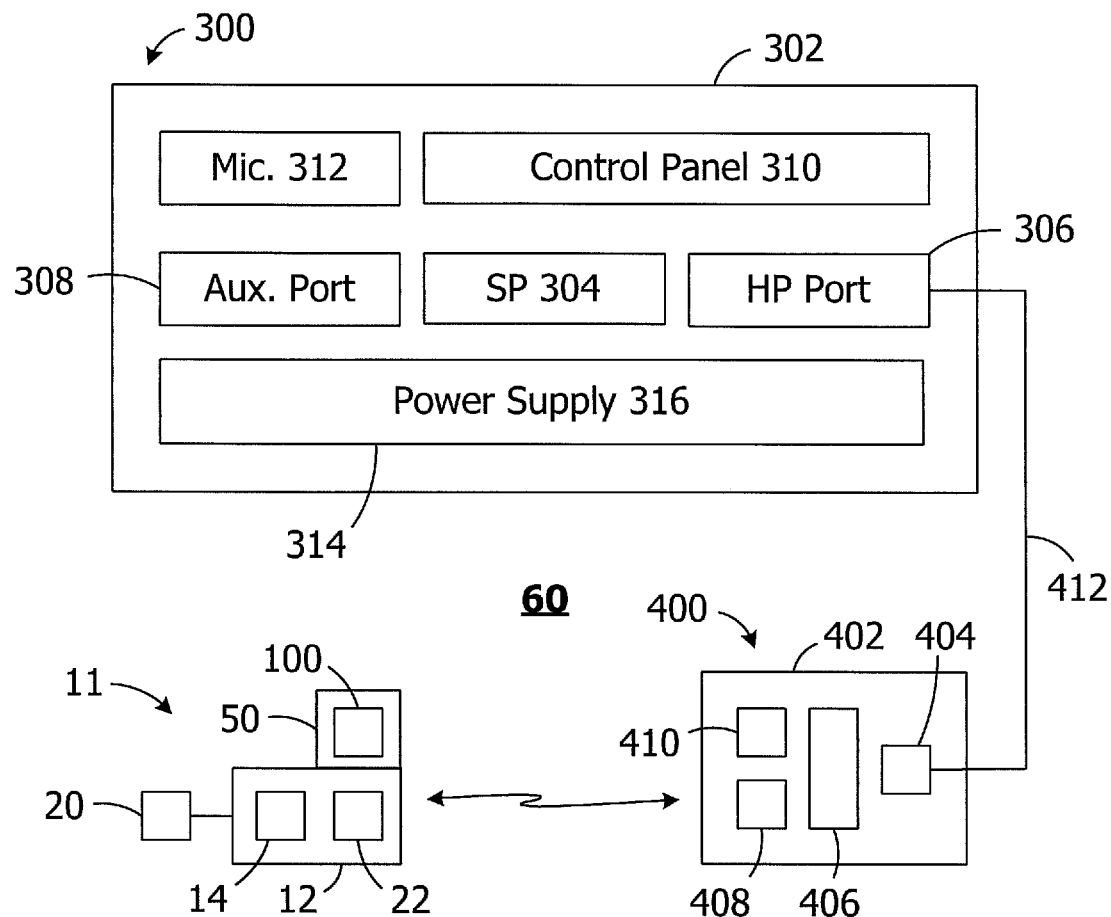
FIG. 25 is a block diagram of a cochlear implant system in accordance with one embodiment of a present invention.
Figure 26:
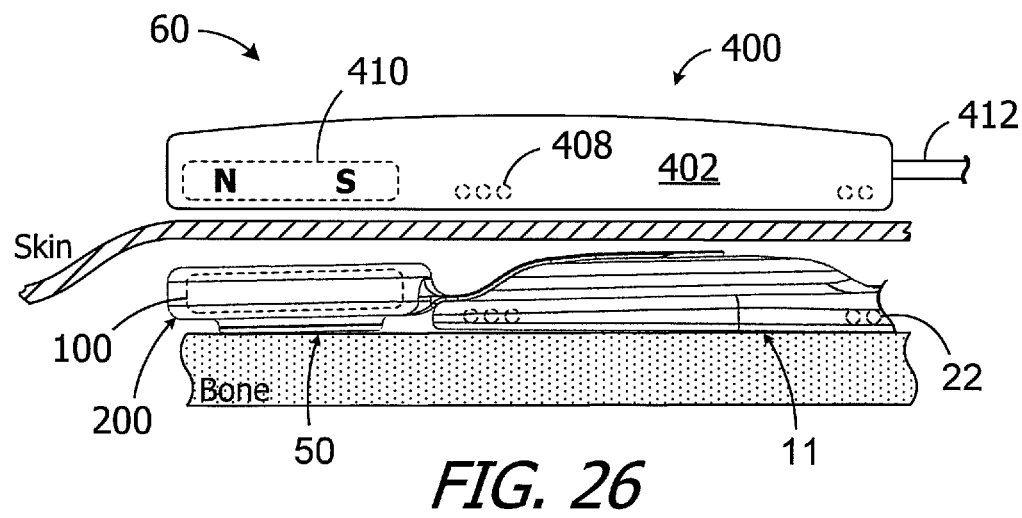
FIG. 26 is side view of a portion of the cochlear implant system illustrated in FIG. 25.

As illustrated in FIGS. 25 and 26, an exemplary ICS system 60 includes the cochlear implant 11, a sound processor such as the illustrated body worn sound processor 300 or a behind-the-ear sound processor, and a headpiece 400 that is configured for use with the cochlear implant 11.

The exemplary body worn sound processor 300 includes a housing 302 in which and/or on which various components are supported. Such components may include, but are not limited to, sound processor circuitry 304, a headpiece port 306, an auxiliary device port 308 for an auxiliary device such as a mobile phone or a music player, a control panel 310, one or more microphones 312, and a power supply receptacle 314 for a removable battery or other removable power supply 316 (e.g., rechargeable and disposable batteries or other electrochemical cells). The sound processor circuitry 304 converts electrical signals from the microphone 312 into stimulation data.

The exemplary headpiece 400 includes a housing 402 and various components, e.g., a RF connector 404, a microphone 406, an antenna (or other transmitter) 408 and a diametrically magnetized disk-shaped positioning magnet 410, that are carried by the housing. The headpiece 400 may be connected to the sound processor headpiece port 306 by a cable 412. The positioning magnet 410 is attracted to the magnet apparatus 100 of the exomagnet 50 of cochlear implant 11, thereby aligning the antenna 408 with the antenna 208. To that end, it should be noted that the locational relationship between the antenna 408 and the magnet 410 is similar to that of the cochlear implant 11, i.e., the magnet is located outside the perimeter defined by the antenna. As a result, the antennas 22 and 408 will be aligned with one another when the magnet 410 is aligned with the magnet apparatus 100 in the manner illustrated in FIG. 26. The stimulation data and, in many instances power, is supplied to the headpiece 400. The headpiece 400 transcutaneously transmits the stimulation data, and in many instances power, to the cochlear implant 11 by way of a wireless link between the antennas. The stimulation processor 14 converts the stimulation data into stimulation signals that stimulate the electrodes of the electrode array 20.

In at least some implementations, the cable 412 will be configured for forward telemetry and power signals at 49 MHz and back telemetry signals at 10.7 MHz. It should be noted that, in other implementations, communication between a sound processor and a headpiece and/or auxiliary device may be accomplished through wireless communication techniques. Additionally, given the presence of the microphone(s) 312 on the sound processor 300, the microphone 406 may be also be omitted in some instances. The functionality of the sound processor 300 and headpiece 400 may also be combined into a single head wearable sound processor. Examples of head wearable sound processors are illustrated and described in U.S. Pat. Nos. 8,811,643 and 8,983,102, which are incorporated herein by reference in their entirety.

Figure 27:
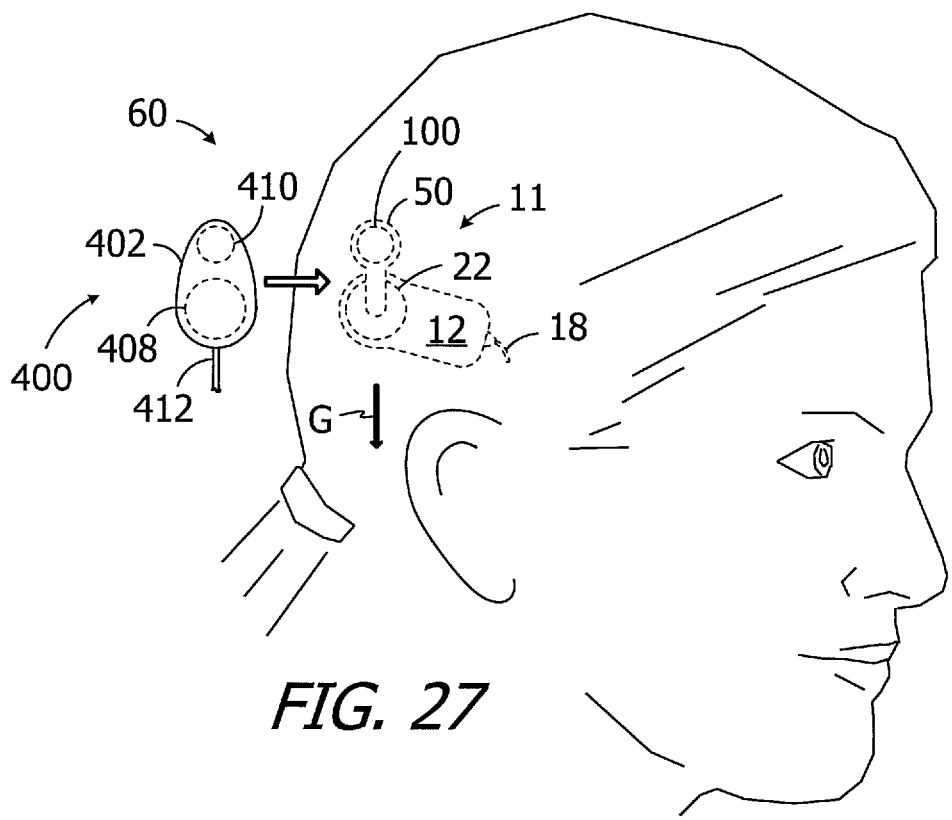
FIG. 27 is a perspective view of an ICS system in accordance with one embodiment of a present invention associated with the right ear of the user.

As noted above, the headpiece 400 should be oriented relative to the cochlear implant 11 in such a manner that the antenna 408 is positioned over and aligned with the antenna 22. One method of ensuring alignment is illustrated in FIG. 27. The exomagent 50 is oriented such that the magnet apparatus 100 is located above the antenna 22, which is offset 90 degrees from the position illustrated in FIG. 26. When the headpiece 400 is placed over the cochlear implant 11, with the positioning magnet 410 aligned with the magnet apparatus 100, the vertical orientation of the headpiece caused by gravitational force G will result in the headpiece antenna 408 being positioned over the implant antenna 22.

Figure 28:
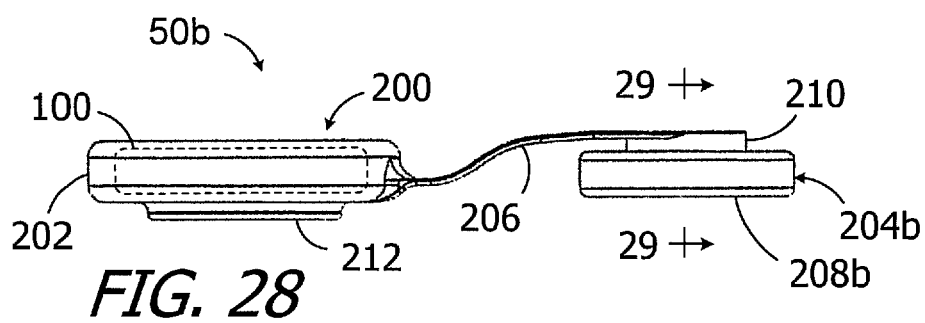
FIG. 28 is a side view of a cochlear implant exomagnet in accordance with one embodiment of a present invention.
Figure 29:
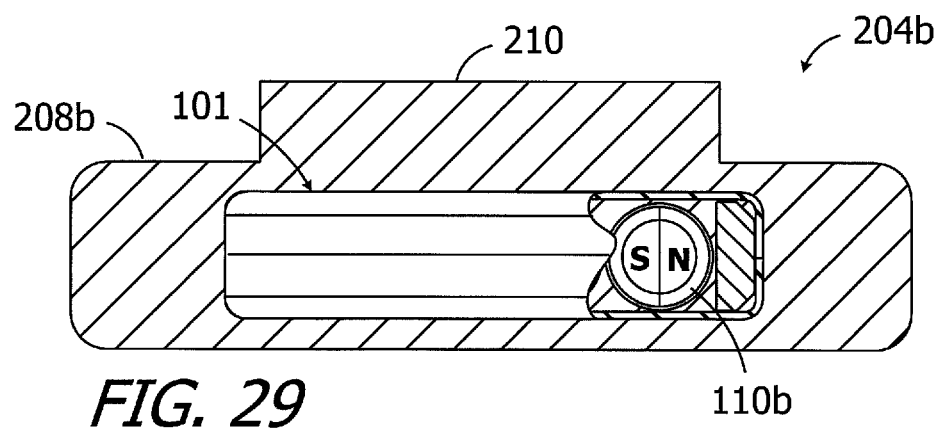
FIG. 29 is a section view take along line 29-29 in FIG. 28.

Orientation magnets may also be used to align the headpiece antenna 408 with the implant antenna 22. To that end, and turning to FIGS. 28 and 29, the exemplary exomagnet 50b is substantially similar to exomagnet 50 and similar elements are represented by similar reference numerals. Here, however, an MRI-compatible orientation magnet apparatus 101 is located within the relatively wide portion 208b of the anchor 204b. The exemplary orientation magnet apparatus 101 is substantially similar to the positioning magnet apparatus 100. The orientation magnet apparatus 101 is, however, smaller and weaker than the positioning magnet apparatus 100. Although the orientation magnet apparatus 101 may be used in the manner described below to control the orientation of a headpiece relative to an implant to align their respective antennas, the orientation magnet apparatus is not strong enough to (on its own) secure the headpiece to the user's head. The orientation magnet apparatus 101 in the illustrated implementation may be about 40-60% smaller than the positioning magnet apparatus 100, may include about 40-60% less magnetic material than the positioning magnet apparatus 100 due to the smaller magnets 110b, and may have about 40-60% less magnetic strength than the positioning magnet apparatus 100. For example, the normal retention force between the positioning magnet apparatus 100 and the headpiece magnet 410 may be about 1.25 N to 1.35 N and the normal retention force between the orientation magnet apparatus 101 (with 6 mm spacing) and the headpiece orientation magnet 411 (FIG. 30) may be about 0.75 N to 0.81 N (with 6 mm spacing).

Figure 30:
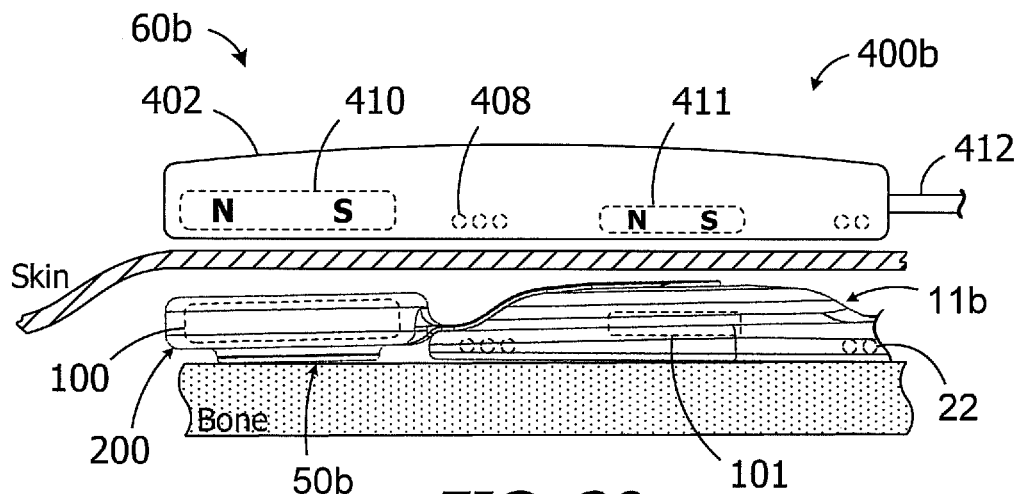
FIG. 30 is side view of a portion of a cochlear implant system in accordance with one embodiment of a present invention.

Referring to FIG. 30, a cochlear implant 11b including the exemplary exomagnet 50b may be combined with a headpiece 400b to form an ICS system 60b. The headpiece 400b is substantially similar to headpiece 400 and similar elements are represented by similar reference numerals. Here, however, the headpiece 400b includes an orientation magnet 411. When the headpiece magnet 410 is placed over the implant positioning magnet apparatus 100 to retain the magnet on the user's head, the attraction between the implant orientation magnet apparatus 101 and the headpiece orientation magnet 411 will align the antennas 22 and 408.

The orientation magnet apparatus 101 may, in other implementations, have a configuration that is different than that of the positioning magnet apparatus 100. For example, the orientation magnet apparatus 101 may have a configuration similar to the magnet apparatus 100a (FIGS. 23 and 24). An orientation magnet apparatus may also be added to the exomagnet 50a (FIGS. 13-16) in some embodiments.

In other exemplary ICS systems, all of the external components (e.g., the battery or batteries, the microphone, the sound processor, and the antenna) are carried within a single headpiece. Various examples of such systems are disclosed in U.S. Pat. No. 8,811,643, which is entitled "Integrated Cochlear Implant Headpiece" and incorporated herein by reference in its entirety. One example of such an ICS system is generally represented by reference numeral 60c in FIG. 31. The headpiece 400c in system 60c includes a housing 402c in which the sound processor 304 (FIG. 25), microphone 312 (FIG. 25), antenna 408, positioning magnet 410, and batteries 316c are located. Here too, when the headpiece 400c is placed over the cochlear implant 11, with the positioning magnet 410 aligned with the magnet apparatus 100, the vertical orientation of the headpiece caused by gravitational force G will result in the headpiece antenna 408 being positioned over the implant antenna 22.

Figure 31:
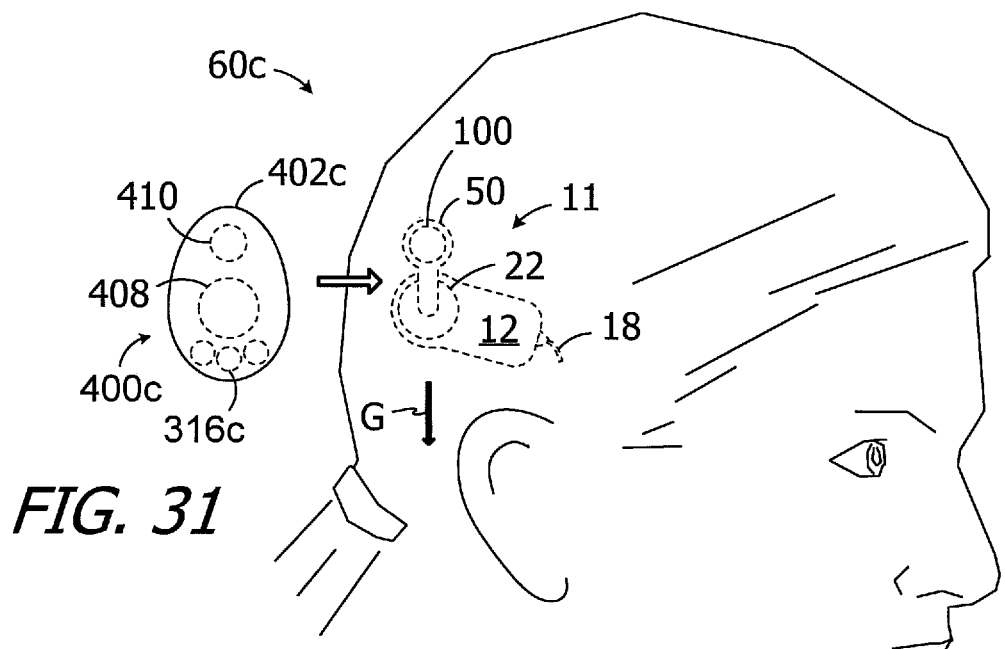
FIG. 31 is a perspective view of an ICS system in accordance with one embodiment of a present invention associated with the right ear of the user.
Figure 32:
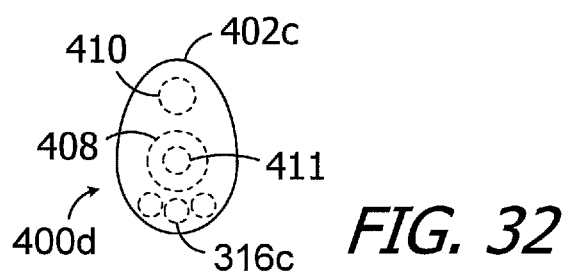
FIG. 32 is a plan view of a headpiece that may be incorporated into the ICS system illustrated in FIG. 31.

The headpiece 400c illustrated in FIG. 31 may also be provided with an orientation magnet. To that end, the headpiece 400d, which is otherwise identical to the headpiece 400c, includes an orientation magnet 411.

Another exemplary exomagnet is generally represented by reference numeral 50e in FIGS. 33-38. The exomagnet 50e is similar to exomagnet 50 and similar elements are represented by similar reference numerals. The exomagnet 50e may also be used in a retrofit method similar to that described above with reference to FIGS. 9 and 10. Here, however, exomagnet 50e is configured to position the associated magnet or magnet apparatus on the outer surface of the top wall of the housing antenna portion instead of on the bone adjacent to the housing antenna portion. So positioned, the associated magnet or magnet apparatus will not be located within the implant housing. In at least some instances, including the illustrated implementation, the associated magnet or magnet apparatus will be centered relative to the antenna that is within the antenna portion.

Figure 33:
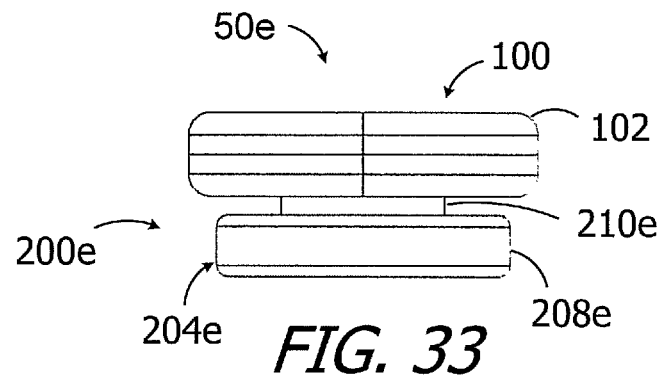
FIG. 33 is a side view of a cochlear implant exomagnet in accordance with one embodiment of a present invention.
Figure 34:
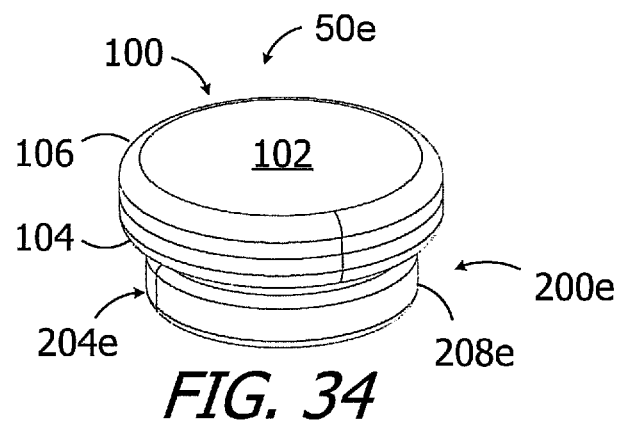
FIG. 34 is a top perspective view of the cochlear implant exomagnet illustrated in FIG. 33.
Figure 35:
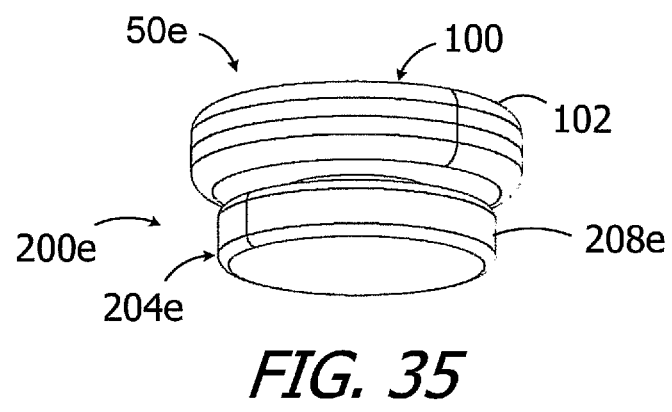
FIG. 35 is a bottom perspective view of the cochlear implant exomagnet illustrated in FIG. 33.

Referring more specifically to FIGS. 33-35, the exemplary exomagnet 50e may include a magnet apparatus, such as the magnet apparatus 100 described above with reference to FIGS. 17-22, and a magnet mount 200e that is configured to be inserted into the internal magnet pocket of the associated cochlear implant. Other exemplary magnet apparatuses include, but are not limited to, the magnet apparatus 100a described above with reference to FIGS. 23 and 24. Magnet apparatuses with disc-shaped magnets, such as the disk-shaped magnets described below with reference to FIGS. 44-52, may also be employed. The exemplary magnet mount 200e includes an anchor 204e with a relatively wide portion 208e that is sized and shaped in a manner corresponding to the magnet pocket of the associated cochlear implant, and a relatively narrow portion 210e that is sized and shaped to extend through the magnet aperture of the associated cochlear implant. The anchor 204e may be permanently connected to the magnet apparatus 100. As used herein, "permanently connected" means that the anchor 204e cannot be removed from the magnet apparatus 100 without destruction of the anchor, the magnet apparatus, or the instrumentality connecting the two (e.g., a weld), and includes anchors that are integral with the magnet apparatus. As used herein, "integral with" means the anchor 204e and at least a portion of the case 102 (e.g., the case base 104) are formed from a single piece of material, as opposed to two or more pieces that are connected to one another with a connecting instrumentality. The anchor 204e, which is permanently connected to the base 104 of the magnet apparatus case 102 in the illustrated embodiment, may be formed from the same material as the case (described above) or the materials used to form the magnet mount 200 (discussed above). Processes such as machining or molding (including metal injection molding) may be employed. Similarly, in those instances where the anchor 204e is integral with the case base 104, both elements may be formed from the case materials described above.

Figure 36:
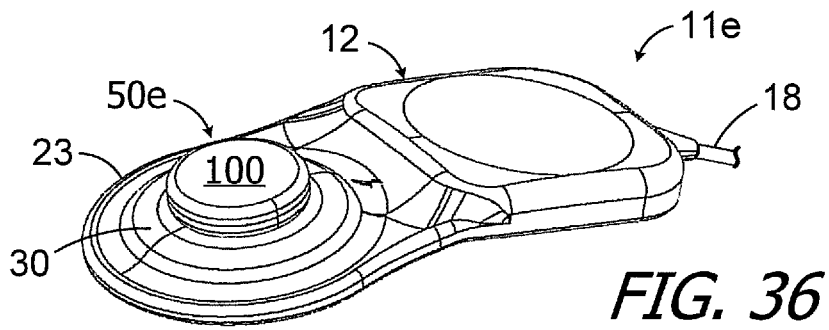
FIG. 36 is a perspective view of a cochlear implant including the exomagnet illustrated in FIG. 33.
Figure 37:
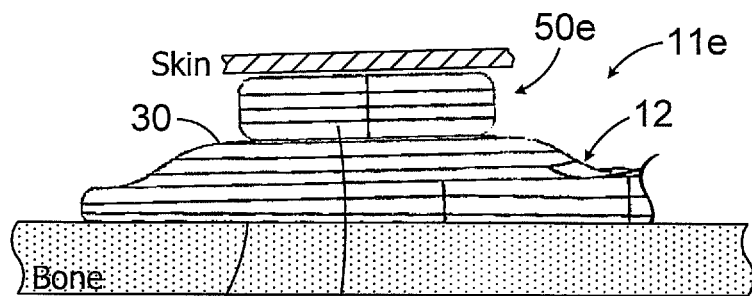
FIG. 37 is a side view of a portion of the cochlear implant illustrated in FIG. 36.
Figure 38:
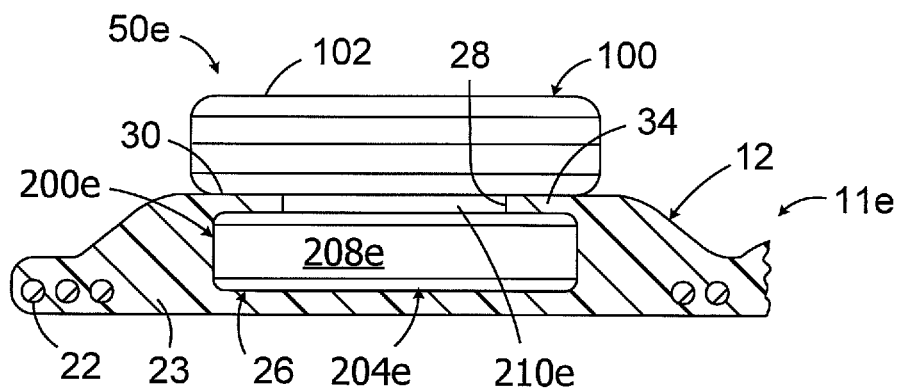
FIG. 38 is a partial section view of a portion of the cochlear implant illustrated in FIG. 36.

Turning to FIGS. 36-38, the cochlear implant 11e is substantially similar to cochlear implant 11 and similar elements are represented by similar reference numerals. Here, however, the cochlear implant 11e includes the exo-magnet 50e which positions the magnet apparatus 100 on the outer surface of the top wall 30 of the cochlear implant housing 12 instead of on the bone adjacent to the housing antenna portion 23. So positioned, the magnet apparatus 100 abuts the inner surface of the skin flap that is over the cochlear implant 11e. As a result, the distance between the magnet apparatus 100 and the associated headpiece magnet (not shown) is decreased, and the magnetic attraction therebetween is increased, as compared to a conventional cochlear implant, such as that illustrated in FIG. 3, due to the presence of the retainer 34 between the magnet 24 and the skin flap when the conventional cochlear implant is employed. The present exomagnet 50e and associated cochlear implant 11e are, therefore, especially useful in those instances where the patient has a particularly thick skin flap.

The exemplary exomagnet generally represented by reference numeral 50f in FIGS. 39-43 is substantially similar to exomagnet 50e and similar elements are represented by similar reference numerals. For example, the exomagnet 50f is configured to position the associated magnet or magnet apparatus on the outer surface of the top wall of the housing antenna portion. Here, however, the anchor and magnet apparatus are not integral with or otherwise permanently connected to one another, and are instead attachable to one another, i.e., configured to be connected to one another during a surgical procedure and disconnected from one another as necessary. As a result, should the surgeon so desire, the anchor may be inserted into the magnet pocket of the associated cochlear implant prior to the magnet apparatus being attached thereto, which may be easier for some surgeons than inserting the anchor into the magnet pocket with the magnet apparatus already attached thereto. Subsequently, the magnet apparatus may be disconnected from the anchor and removed from the patient (e.g., prior to an MRI procedure) while the anchor, which occupies the entire magnet pocket, remains within the magnet pocket to prevent fibrosis and/or the ingress of bacteria. In other words, the anchor functions as a so-called "dummy" magnet.

Figure 39:
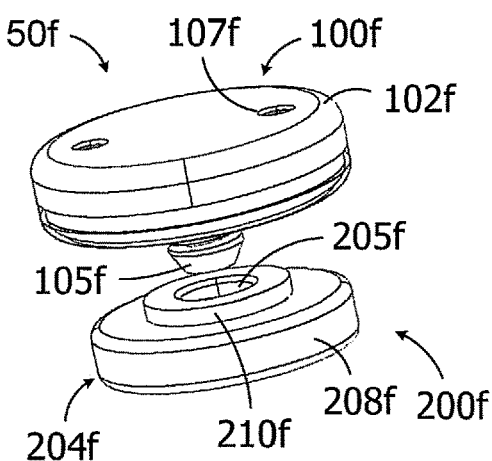
FIG. 39 is an exploded perspective view of a cochlear implant exomagnet in accordance with one embodiment of a present invention.
Figure 40:
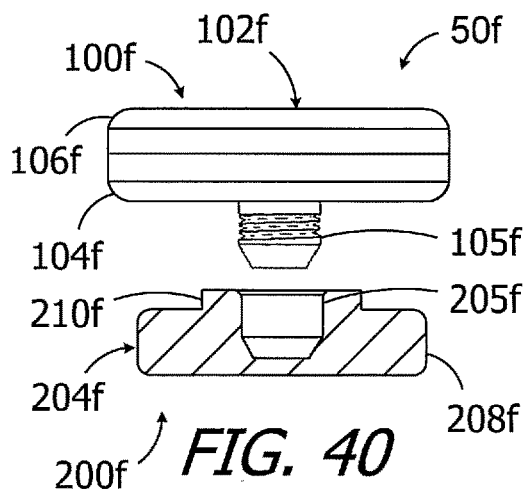
FIG. 40 is an exploded partial section view of the cochlear implant exomagnet illustrated in FIG. 39.

Referring first to FIGS. 39 and 40, the exemplary exomagnet 50f may include a magnet apparatus 100f, with a case 102f and in some instances the same internal components as the magnet apparatus 100 (FIG. 17-22) or the magnet apparatus 100a (FIGS. 23-24), and a magnet mount 200f with an anchor 204f. The anchor 204f includes a relatively wide portion 208f that is sized and shaped in a manner corresponding to the magnet pocket of the associated cochlear implant, and a relatively narrow portion 210f that is sized and shaped to extend through the magnet aperture of the associated cochlear implant. The magnet apparatus 100f and the anchor 204f, which are configured to be attached to one another during the surgical procedure, also include respective fastener members 105f and 205f. In the illustrated embodiment, the fastener member 105f is a screw or other threaded structure and the faster member 205f is a threaded receptacle. In other embodiments (not shown), the fastener member 105f may be a threaded receptacle post and the faster member 205f may be a screw or other threaded structure.

Figure 39A:
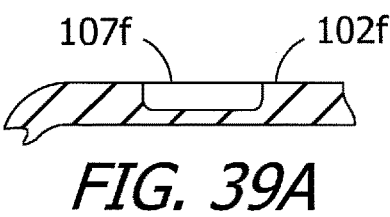
FIG. 39A is a section view of a portion of the cochlear implant exomagnet illustrated in FIG. 39.

The exemplary case 102f may include one or more tool receptacles to facilitate rotation of the magnet apparatus 100f when the magnet apparatus is being secured to the anchor 204f. The tool receptacles extend partially, and not completely, through the top wall of the case 102f (FIG. 39A) and may be in the form of the illustrated diametrically spaced pair of cylindrical tool receptacles 107f. Tool receptacles of other shapes and sizes, such as a single linear receptacle or a hexagonal receptacle, may also be employed.

Figure 41:
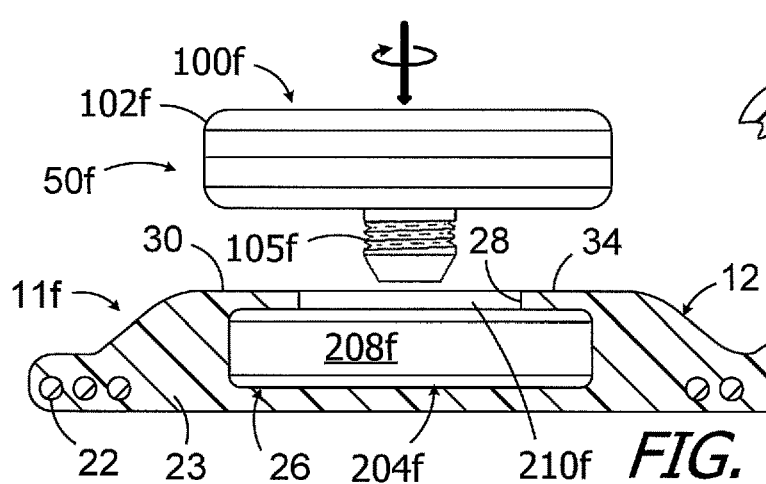
FIG. 41 is an exploded partial section view of a cochlear implant including the exomagnet illustrated in FIG. 39 being assembled.
Figure 42:
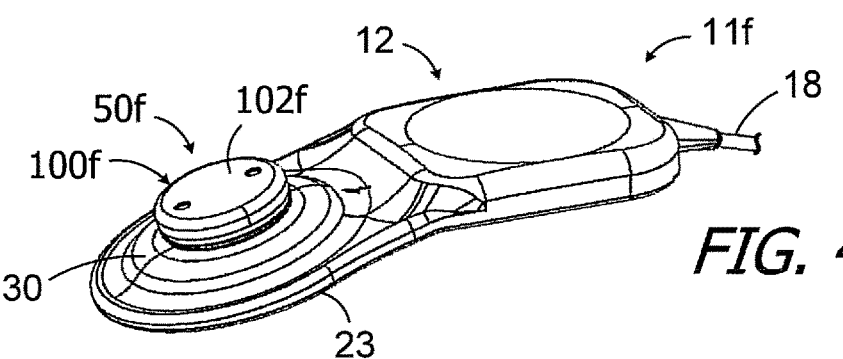
FIG. 42 is a perspective view of the cochlear implant illustrated in FIG. 41.
Figure 43:
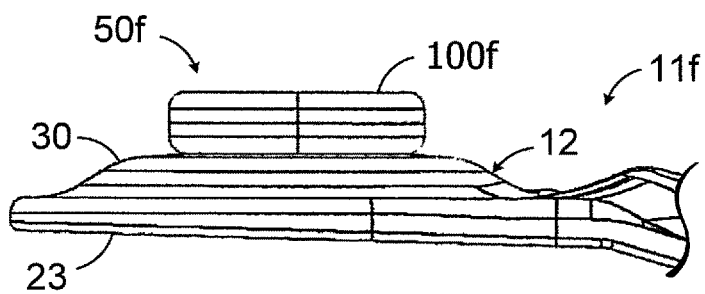
FIG. 43 is a side view of a portion of the cochlear implant illustrated in FIG. 41.

As illustrated for example in FIG. 41, the anchor 204f may be inserted into the magnet pocket 26 prior to the magnet apparatus 100f being secured to the anchor. The magnet apparatus 100f may then be secured to anchor 204f by placing the threaded structure 105f into the threaded receptacle 205f and rotating the magnet apparatus relative to the anchor. Such rotation may continue until the magnet apparatus 100f is against the housing top wall 30 (FIGS. 42-43), thereby completing the cochlear implant 11f.

Figure 44:
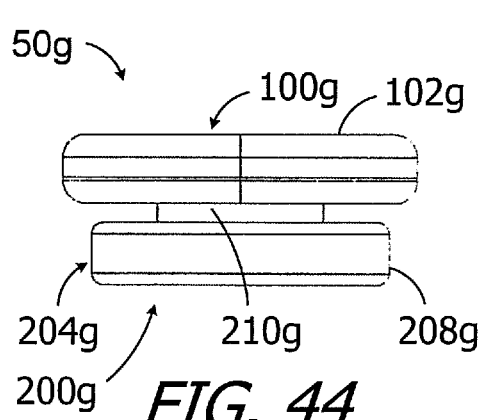
FIG. 44 is a side view of a cochlear implant exomagnet in accordance with one embodiment of a present invention.
Figure 45:
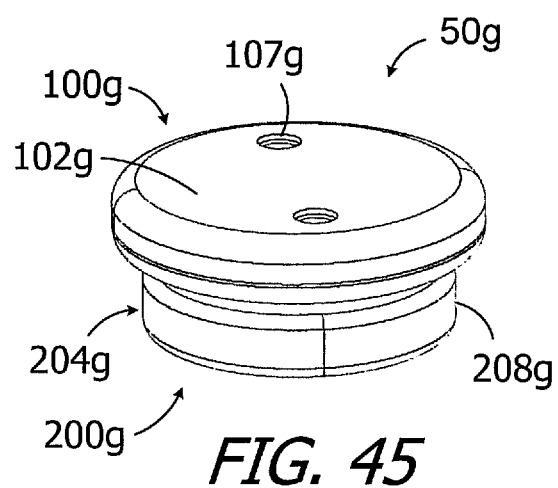
FIG. 45 is a perspective view of the cochlear implant exomagnet illustrated in FIG. 44.
Figure 46:
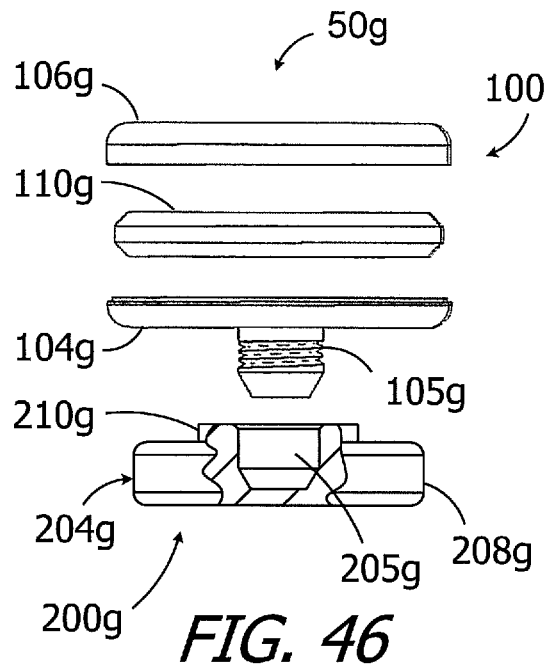
FIG. 46 is an exploded view of the cochlear implant exomagnet illustrated in FIG. 44.

Another exemplary exomagnet is generally represented by reference numeral 50g in FIGS. 44-46. The exomagnet 50g is substantially similar to exomagnet 50f and similar elements are represented by similar reference numerals. For example, the exomagnet 50g includes a magnet apparatus 100g with housing 102g and a fastener member 105g. The housing 102g has a base 104g, a cover 106g and a pair of tool receptacles 107g. The exemplary magnet mount 200g includes an anchor 204g with a relatively wide portion 208g that is sized and shaped in a manner corresponding to the magnet pocket of the associated cochlear implant, a relatively narrow portion 210g that is sized and shaped to extend through the magnet aperture of the associated cochlear implant, and a fastener member 205g. The magnet apparatus 100g does not, however, including the internal components illustrated in FIGS. 18-21 and instead includes a single diametrically magnetized disc-shaped magnet 110g. The use of a disc-shaped magnet results in a magnet apparatus that is thinner than a magnet apparatus such as magnet apparatus 100 with the internal components illustrated in FIGS. 18-21.

Figure 47:
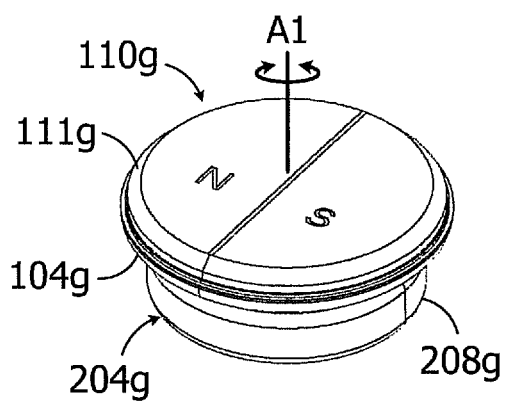
FIG. 47 is a perspective view of a portion of the cochlear implant exomagnet illustrated in FIG. 44.
Figure 48:
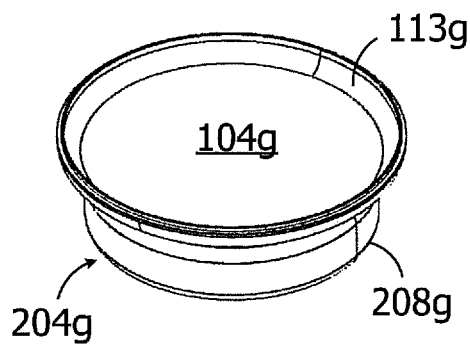
FIG. 48 is a perspective view of a portion of the cochlear implant exomagnet illustrated in FIG. 44.

As illustrated for example in FIG. 47, the exemplary magnet 110g is rotatable within the case 102g about axis A.

The exemplary magnet 110g also includes chamfered edges 111g. The case base 104g includes a corresponding chamfered inner surface 113g and the case cover 106g includes a similar chamfered inner surface (not shown).

Figure 49:
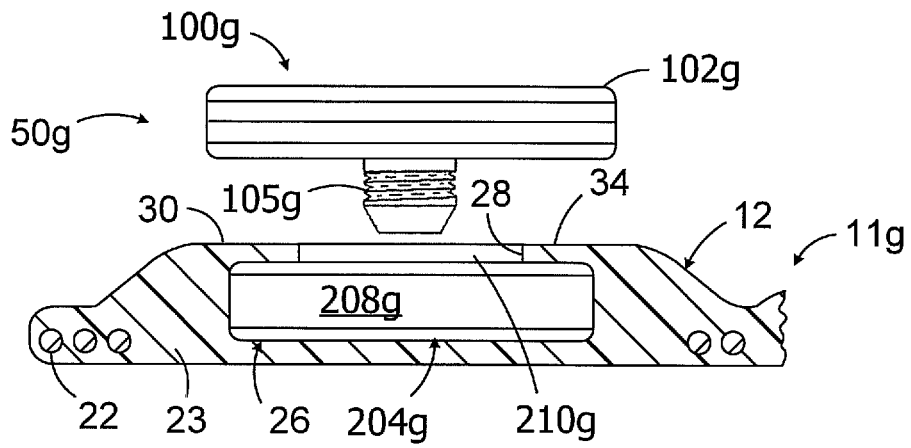
FIG. 49 is an exploded partial section view of a cochlear implant including the exomagnet illustrated in FIG. 44 being assembled.
Figure 50:
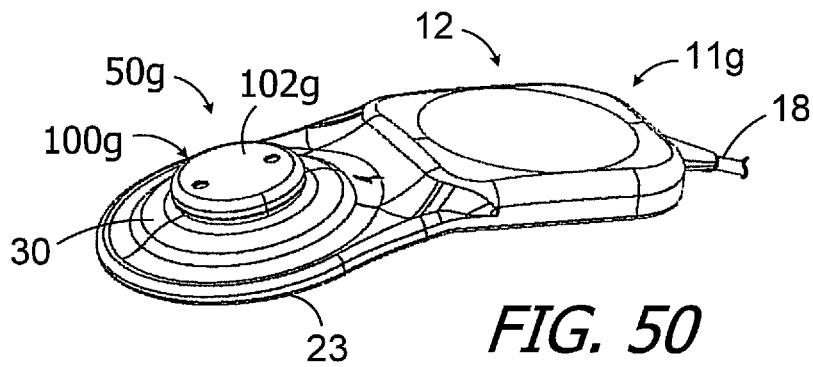
FIG. 50 is a perspective view of a cochlear implant including the exomagnet illustrated in FIG. 44.

Turning to FIGS. 49 and 50, the anchor 204g may be inserted into the magnet pocket 26 prior to the magnet apparatus 100g being secured to the anchor. The magnet apparatus 100g may then be secured to anchor 204g by placing the threaded structure 105g into the threaded receptacle 205g (FIG. 46) and rotating the magnet apparatus relative to the anchor. Such rotation may continue until the magnet apparatus 100g against the housing top wall 30 (FIG. 50), thereby completing the cochlear implant 11g.

Figure 51:
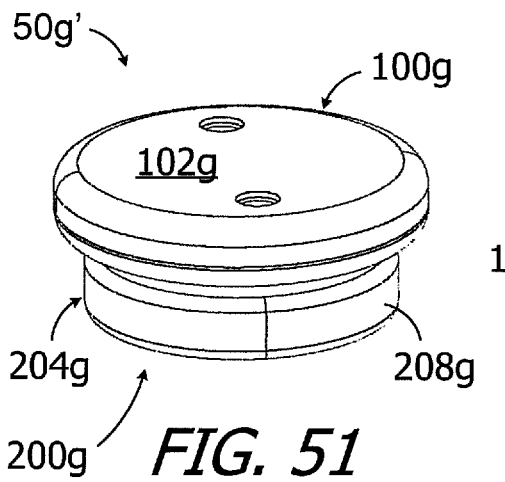
FIG. 51 is a perspective view of a cochlear implant exomagnet in accordance with one embodiment of a present invention.
Figure 52:
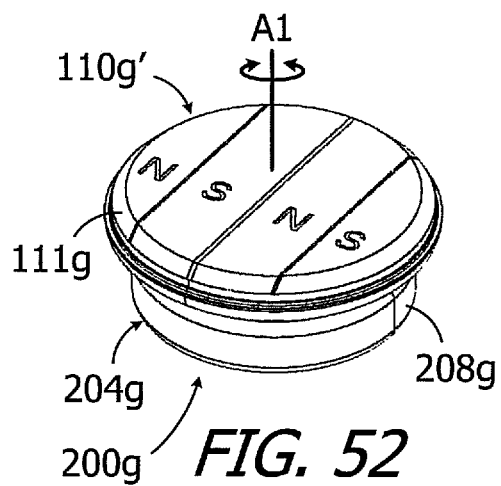
FIG. 52 is a perspective view of a portion of the cochlear implant exomagnet illustrated in FIG. 51.
Figure 53:
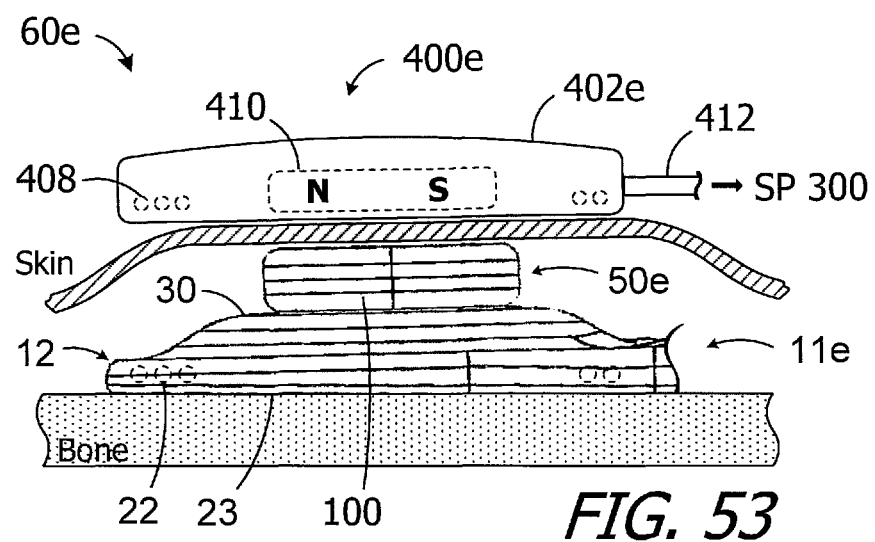
FIG. 53 is a side view of a portion of a cochlear implant system in accordance with one embodiment of a present invention.

Another exemplary exomagnet is generally represented by reference numeral 50g' in FIG. 51. The exomagnet 50g' is identical to the exomagnet 50g but for the configuration of the disc-shaped magnet 110g' illustrated in FIG. 52, which has a striped N-S-N-S pole configuration as opposed to the N-S pole configuration of the magnet 110g (FIG. 47).

The exemplary cochlear implants 11e-11g may be incorporated into ICS systems otherwise conventional cochlear implant systems. For example, the cochlear implant system 60e illustrated in FIG. 53 includes the cochlear implant 11e, the above-described sound processor 300 (FIG. 25), and a headpiece 400e. The headpiece 400e includes a housing 402e, and components such as a RF connector (not shown), a microphone (not shown), an antenna (or other transmitter) 408 and a diametrically magnetized disk-shaped positioning magnet 410, that are carried by the housing. The headpiece 400e may be connected to the sound processor 300 by a cable 412. The positioning magnet 410 is attracted to the magnet apparatus 100 of the exomagnet 50e of cochlear implant 11e, thereby aligning the headpiece antenna 408 with the implant antenna 22.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A cochlear implant exomagnet for use with a cochlear implant, the cochlear implant having an implant housing with an internal magnet pocket and an antenna adjacent to the internal magnet pocket, the exomagnet comprising:
   a magnet apparatus; and
   a magnet mount configured to secure the magnet apparatus to the cochlear implant in such a manner that the magnet apparatus is not located within the internal magnet pocket.

2. A cochlear implant exomagnet as claimed in claim 1, wherein
   the magnet apparatus comprises a MRI-compatible magnet apparatus.

3. A cochlear implant exomagnet as claimed in claim 1, wherein
   the magnet apparatus comprises a case defining a central axis, a magnet frame within the case and rotatable about the central axis of the case, and a plurality of elongate diametrically magnetized magnets that are located in the magnet frame, the magnets defining a longitudinal axis and a N-S direction and being freely rotatable about the longitudinal axis relative to the magnet frame.

4. A cochlear implant exomagnet as claimed in claim 1, wherein
   the magnet mount includes a housing in which the magnet apparatus is located and an anchor configured to occupy the internal magnet pocket.

5. A cochlear implant exomagnet as claimed in claim 4, further comprising:
   a flexible connector that extends from the magnet mount housing to the anchor.

6. A cochlear implant exomagnet as claimed in claim 4, wherein
   the anchor comprises a disk-shaped anchor.

7. A cochlear implant exomagnet as claimed in claim 4, wherein
   the magnet mount housing includes at least one tab with an aperture that is configured to receive a bone screw.

8. A cochlear implant exomagnet as claimed in claim 4, wherein
   the implant housing is formed from a material having a first hardness; and
   the anchor is formed from a material having a second hardness that is greater than the first hardness.

9. A cochlear implant exomagnet as claimed in claim 4, wherein
   the magnet apparatus comprises a positioning magnet apparatus having a first magnetic strength; and
   the anchor includes an orientation magnet apparatus having a second magnetic strength that is less than the first magnetic strength.

10. A cochlear implant exomagnet as claimed in claim 1, wherein
    the implant housing includes an antenna portion; and
    the magnet mount is configured to secure the magnet apparatus to the cochlear implant in such a manner that the magnet apparatus is located beyond, but adjacent to, the antenna portion of the implant housing.

11. A cochlear implant exomagnet as claimed in 10 claim 1, wherein
    the magnet mount is formed from a silicone elastomer.

12. A cochlear implant exomagnet as claimed in claim 1, wherein
    the magnet mount includes an anchor configured to occupy the internal magnet pocket.

13. A cochlear implant exomagnet as claimed in claim 12, wherein
    the implant housing includes an antenna portion with an outer surface; and
    the magnet mount is configured to secure the magnet apparatus to the cochlear implant in such a manner that the magnet apparatus is located on the outer surface of the antenna portion of the implant housing and is centered relative to the antenna.

14. A cochlear implant exomagnet as claimed in claim 12, wherein
    the anchor is permanently connected to the magnet apparatus.

15. A cochlear implant exomagnet as claimed in claim 12, wherein
    the anchor and the magnet apparatus are configured to be connected to one another during a surgical procedure.

16. A cochlear implant exomagnet as claimed in claim 1, wherein the magnet apparatus includes a case with at least one tool receptacle and one or more magnets or magnetic material particles within the case.

17. A cochlear implant, comprising
a cochlear lead including a plurality of electrodes;
an implant housing including a magnet pocket in which no implant magnet is located;
an antenna within the implant housing;
a stimulation processor operably connected to the antenna and to the cochlear lead; and
an exomagnet as claimed in claim 1 secured to the implant housing at the magnet pocket.

18. A system, comprising
a cochlear lead including a plurality of electrodes;
an implant housing including a magnet pocket in which no implant magnet is located;
an antenna within the implant housing;
a stimulation processor operably connected to the antenna and to the cochlear lead;
an exomagnet as claimed in claim 1 secured to the implant housing at the magnet pocket; and
a headpiece including an antenna defining a perimeter and a headpiece magnet located outside the perimeter that is attracted to the magnet apparatus of the exomagnet.

19. A system as claimed in claim 17, further comprising a sound processor operably connected to the headpiece.

20. A cochlear implant exomagnet for use with a cochlear implant, the cochlear implant having an implant housing with an internal magnet pocket and an antenna adjacent to the internal magnet pocket, the exomagnet comprising:
a magnet apparatus; and
means for anchoring the magnet apparatus to the internal magnet pocket in such a manner that the magnet apparatus is not located within the internal magnet pocket.

21. A cochlear implant exomagnet as claimed in claim 20, wherein
the magnet apparatus comprises a MRI-compatible magnet apparatus.

22. A cochlear implant exomagnet as claimed in claim 20, wherein
the magnet apparatus comprises a case defining a central axis, a magnet frame within the case and rotatable about the central axis of the case, and a plurality of elongate diametrically magnetized magnets that are located in the magnet frame, the magnets defining a longitudinal axis and a N-S direction and being freely rotatable about the longitudinal axis relative to the magnet frame.

23. A cochlear implant exomagnet as claimed in claim 20, wherein
the magnet apparatus comprises a positioning magnet apparatus having a first magnetic strength; and
the exomagnet further comprises an orientation magnet apparatus having a second magnetic strength that is less than the first magnetic strength, and
the means for anchoring anchors the orientation magnet apparatus within the internal magnet pocket.

* * * * *